(12) United States Patent
Chiattello et al.

(10) Patent No.: US 10,212,932 B2
(45) Date of Patent: Feb. 26, 2019

(54) ANTIMICROBIAL PHOTOREACTIVE COMPOSITION COMPRISING ORGANIC AND INORGANIC MULTIJUNCTION COMPOSITE

(71) Applicant: eXion labs Inc., West Des Moines, IA (US)

(72) Inventors: Marion L. Chiattello, Cedar Falls, IA (US); Mark Oman, West Des Moines, IA (US)

(73) Assignee: eXion Labs Inc., West Des Moines, IA (US)

( * ) Notice: Subject to any disclaimer, the term of this patent is extended or adjusted under 35 U.S.C. 154(b) by 0 days.

(21) Appl. No.: 15/662,068

(22) Filed: Jul. 27, 2017

(65) Prior Publication Data
US 2018/0027809 A1 Feb. 1, 2018

Related U.S. Application Data

(60) Provisional application No. 62/367,981, filed on Jul. 28, 2016, provisional application No. 62/488,438, filed on Apr. 21, 2017.

(51) Int. Cl.
*A01N 33/04* (2006.01)
*A01N 25/02* (2006.01)
(Continued)

(52) U.S. Cl.
CPC ............ *A01N 33/04* (2013.01); *A01N 25/00* (2013.01); *A01N 25/02* (2013.01); *A01N 33/12* (2013.01);
(Continued)

(58) Field of Classification Search
CPC ........ A01N 25/00; A01N 25/02; A01N 33/04; A01N 33/12; A01N 37/18; A01N 55/02;
(Continued)

(56) References Cited

U.S. PATENT DOCUMENTS 6,645,307 B2 11/2003 Fox et al.
7,438,767 B2 10/2008 Mckechnie et al.
(Continued)

FOREIGN PATENT DOCUMENTS

CN 105728010 A 7/2016
CN 106590976 A 4/2017
(Continued)

OTHER PUBLICATIONS

Liu, Yangquiao et al., "In situ coating multiwalled carbon nanotubes with CdS nanoparticles," Materials Chemistry and Physics 91 (2005) 365-369 (Year: 2005).*

(Continued)

*Primary Examiner* — Timothy C Cleveland
(74) *Attorney, Agent, or Firm* — Leydig, Voit & Mayer, Ltd.

(57) ABSTRACT

Provided is an antimicrobial photoreactive composition comprising a photocatalytic multijunction composite that is photoreactive in ordinary room lighting and comprises at least one photocatalytic heterojunction that is primarily carbon based. The composition further comprises at least one surface-coupling material, optionally at least one additive selected from a charge-transfer augmenting material, a light-capturing augmenting material, an antimicrobial augmenting material(s), or a combination thereof, and a carrier. The composition can be coupled to a surface or embedded in a cationic polymer matrix to form an antimicrobial film that is removable. Further provided is a method of disinfecting a surface comprising applying the antimicrobial photoreactive composition to a surface.

28 Claims, 4 Drawing Sheets

(51) Int. Cl.
| | |
|---|---|
| A01N 33/12 | (2006.01) |
| A01N 37/18 | (2006.01) |
| A61L 2/18 | (2006.01) |
| B01J 27/24 | (2006.01) |
| B01J 31/02 | (2006.01) |
| B01J 31/06 | (2006.01) |
| B01J 35/00 | (2006.01) |
| A01N 25/00 | (2006.01) |
| A01N 55/02 | (2006.01) |
| A01N 59/16 | (2006.01) |

(52) U.S. Cl.
CPC ............ *A01N 37/18* (2013.01); *A01N 55/02* (2013.01); *A01N 59/16* (2013.01); *A61L 2/18* (2013.01); *B01J 27/24* (2013.01); *B01J 31/0208* (2013.01); *B01J 31/06* (2013.01); *B01J 35/004* (2013.01)

(58) Field of Classification Search
CPC ......... A01N 59/16; A61L 2/18; A61L 2/0284; B01J 27/24; B01J 31/0208; B01J 31/06; B01J 35/004
See application file for complete search history.

(56) References Cited

U.S. PATENT DOCUMENTS

| | | |
|---|---|---|
| 2004/0157757 A1 | 8/2004 | Massholder |
| 2010/0034770 A1 | 2/2010 | Mize |
| 2010/0062966 A1 | 3/2010 | Lincoln et al. |
| 2011/0073688 A1 | 3/2011 | Yang |
| 2012/0132930 A1 | 5/2012 | Young et al. |
| 2014/0316180 A1 | 10/2014 | Fomitchev-Zamilov |
| 2015/0275144 A1 | 10/2015 | Hulskotter et al. |
| 2016/0143294 A1 | 5/2016 | Bond |

FOREIGN PATENT DOCUMENTS

| | | |
|---|---|---|
| CN | 106752446 A | 5/2017 |
| WO | WO 2008/128827 A1 | 10/2008 |
| WO | WO 2011/044580 A2 | 4/2011 |
| WO | WO 2014/207655 A1 | 12/2014 |
| WO | WO 2015/091261 A1 | 6/2015 |
| WO | WO 2017/053466 A1 | 3/2017 |

OTHER PUBLICATIONS

Korean Intellectual Property Office, International Search Report and Written Opinion in International Application No. PCT/US2017/044216, dated Nov. 8, 2017.
Aerts et al., "Highly efficient carrier multiplication in PbS nanosheets," *Nature Communications*, 5: 3789, pp. 1-5 (2014).
Ayan-Varela et al., "Investigating the Dispersion Behavior in Solvents, Biocompatibility, and Use as Support for Highly Efficient Metal Catalysts of Exfoliated Graphitic Carbon Nitride," *ACS Appl. Mater. Interfaces*, 7: 24032-24045 (2015).
Ayan-Varela et al., "Achieving Extremely Concentrated Aqueous Dispersions of Graphene Flakes and Catalytically Efficient Graphene-Metal Nanoparticle Hybrids with Flavin Mononucleotide as a High-Performance Stabilizer," *ACS Appl. Mater. Interfaces*, 7: 10293-10307 (2015).
Bai et al., "Photocatalytic Activity Enhanced via g-$C_3N_4$ Nanoplates to Nanorods," *J. Phys. Chem. C*, 117: 9952-9961 (2013).
Bai et al., "Photocatalytic Performance Enhanced via P3HT-g-$C_3N_4$ Heterojunction," *J. Mater. Chem. A*, S1-S6 (Supporting Information) (2014).
Bai et al., "Enhancement of photocatalytic performance via a P3HT-g-$C_3N_4$ heterojunction," *J. Mater. Chem. A*, 3: 2741-2747 (2015).
Baird, "Nano-particle dispersion technique improves polymers," *Phys.Org.*, 6085: 1-2 (2005).
Blankenburg et al., "TPD wide-bandgap polymers for solar cell application and their sensitization with small molecule dyes," *Synthetic Metals*, 199: 93-104 (2015).
Boonprakob et al., "Enhanced visible-light photocatalytic activity of g-$C_3N_4$/$TiO_2$ films," *J. Colloid and Interface Science*, 417: 402-409 (2014).
Chai et al., "Graphitic carbon nitride (g-$C_3N_4$)—Pt-$TiO_2$ nanocomposite as an efficient photocatalyst for hydrogen production under visible light irradiation," *Phys. Chem. Chem. Phys.*, 14: 16745-16752 (2012).
Chang et al., "High-Performance Organic Materials for Dye-Sensitized Solar Cells: Triarylene-Linked Dyads with a 4-tert-Butylphenylamine Donor," *Chem. Asian. J.*, 11 pgs. (2011).
Chen et al., "Surface Functionalization of g-$C_3N_4$: Molecular-Level Design of Noble-Metal-Free Hydrogen Evolution Photocatalysts," *Chem. Eur. J.*, 21: 1-6 (2015).
Cheng et al., "The amphoteric properties of g—$C_3N_4$ nanosheets and fabrication of their relevant heterostructure photocatalysts by an electrostatic re-assembly route," *Chem. Commun.*, 51: 7176-7179 (2015).
Cho et al., "Different Inactivation Behaviors of MS-2 Phage and *Escherichia coli* in $TiO_2$ Photocatalytic Disinfection," *Applied and Environmental Microbiology*, 71(1): 270-275 (2005).
Dharmadasa et al., "New ways of developing glass / conducting glass / CdS / CdTe / metal thin-film solar cells based on a new model," *Semicond. Sci. Technol.*, 17: 1238-1248 (2002).
Dong et al., "In Situ Construction of g-$C_3N_4$/g-$C_3N_4$ Metal-Free Heterojunction for Enhanced Visible-Light Photocatalysis," *ACS Appl. Mater. Interfaces*, 5: 11392-11401 (2013).
Dong et al., "Carbon self-doping induced high electronic conductivity and photoreactivity of g-$C_3N_4$," *Chem. Commun.*, 48: 6178-6180 (2012).
Dong et al., "A fantastic graphitic carbon nitride (g-$C_3N_4$) material: Electronic structure, photocatalytic and photoelectronic properties," *Journal of Photochemistry and Photobiology C: Photochemistry Reviews*, 20: 33-50 (2014).
Dou et al., "Low-Bandgap Near-IR Conjugated Polymers/Molecules for Organic Electronics," *Chem. Rev.*,115: 12633-12665 (2015).
Du et al., "A scalable chemical route to soluble acidified graphitic carbon nitride: an ideal precursor for isolated ultrathin g-$C_3N_4$ nanosheets," *Nanoscale*, 7: 8701-8706 (2015).
Fan et al., "Improved photocatalytic activity of g-$C_3N_4$ derived from cyanamide-urea solution," *RSC Adv.*, 5: 8323-8328 (2015).
Fu et al., "Growth of g-$C_3N_4$ Layer on Commercial $TiO_2$ for Enhanced Visible Light Photocatalytic Activity," *Journal of Nanomaterials*, 869094: 1-8 (2014).
Gao et al., "Ion coordination significantly enhances the photocatalytic activity of graphitic-phase carbon nitride," *Dalton Trans.*, 43: 8178-8183 (2014).
Grinou et al., "Dispersion of Pt Nanoparticle-Doped Reduced Graphene Oxide Using Aniline as a Stabilizer," *Materials*, 5: 2927-2936 (2012).
Hu et al., "Properties and photocatalytic performance of polypyrrole and polythiophene modified g-$C_3N_4$nananocomposites," *RSC Adv.*, 5: 31947-31953 (2015).
Jo et al., "Enhanced visible light-driven photocatalytic performance of ZnO-g-$C_3N_4$ , coupled with graphene oxide as a novel ternary nanocomposite," *Journal of Hazardous Materials*, 299: 462-470 (2015).
Li et al., "Direct Transformation from Graphitic $C_3N_4$ to Nitrogen-Doped Graphene: An Efficient Metal-Free Electrocatalyst for Oxygen Reduction Reaction," *ACS Appl. Mater. Interfaces*, 7: 19626-19634 (2015).
Li et al., "A facile synthesis of g-$C_3N_4$/$TiO_2$ hybrid photocatalysts by sol-gel method and its enhanced photodegradation towards methylene blue under visible light," *Advanced Powder Technology*, 27: 330-337 (2015).
Li et al., "Mechanism of NO Photocatalytic Oxidation on g-$C_3N_4$ Was Changed by Pd-QDs Modification," *Molecules*, 21(36): 1-10 (Dec. 26, 2015).

(56) References Cited

OTHER PUBLICATIONS

Li et al., "Enhanced Photocatalytic Performance of Luminescent g-$C_3N_4$ Photocatalyst in Darkroom," *Nanoscale Res. Lett.*, 11:91, 10 pgs. (Feb. 16, 2016).
Li et al., "Graphene/g-$C_3N_4$ bilayer: considerable band gap opening and effective band structure engineering," *Phys. Chem. Chem. Phys.*, 16: 4230-4235 (2014).
Li et al., "Facile synthesis of sheet-like N—$TiO_2$/g-$C_3N_4$ heterojunctions with highly enhanced and stable visible-light photocatalytic activities," *RSC Adv.*, 5: 34281-34291 (2015).
Li et al., "Cross-Linked g-$C_3N_4$/rGO Nanocomposites with Tunable Band Structure and Enhanced Visible Light Photocatalytic Activity," *Small*, 9(19): 3336-3344 (2013).
Liang et al., "Holey Graphitic Carbon Nitride Nanosheets with Carbon Vacancies for Highly Improved Photocatalytic Hydrogen Production," *Adv. Funct. Mater.*, 25: 6885-6892 (2015).
Liao et al., "Graphene oxide modified g-$C_3N_4$ hybrid with enhanced photocatalytic capability under visible light irradiation," *J. Mater. Chem.* 22: 2721-2726 (2012).
Liao et al., "A facile method of activating graphitic carbon nitride for enhanced photocatalytic activity," *Phys. Chem. Chem. Phys.*, 17: 27826-27832 (2015).
Lin et al., "Facile Synthesis of Nitrogen-Doped Graphene via Pyrolysis of Graphene Oxide and Urea, and its Electrocatalytic Activity toward the Oxygen-Reduction Reaction," *Adv. Energy Mater.*, 2(7): 884-888 (2012).
Liu et al., "Graphitic carbon nitride 'reloaded': emerging applications beyond (photo)catalysis," *Chem. Soc. Rev.*, 45: 2308-2326 (2016).
Liu, "Origin of High Photocatalytic Efficiency in Monolayer g-$C_3N_4$/CdS Heterostructure: A Hybrid DFT Study," *J. Phys. Chem. C*, 119: 28417-28423 (2015).
Liu et al., "Enhanced Disperson of $TiO_2$ Nanoparticles in a $TiO_2$/PEDOT:PSS Hybrid Nanocomposite via Plasma-Liquid interactions," *Scientific Reports*, 5 (15765): 1-11 (2015).
Ma et al., "Enhanced photocatalytic oxidation of NO over g-$C_3N_4$-TiO2 under UV and visible light," *Applied Catalysis B: Environmental*, 184: 28-34 (2016) (published online Nov. 19, 2015).
Mamba at al., "Graphitic carbon nitride (g-$C_3N_4$) nanocomposites: A new and exciting generation of visible light driven photocatalysts for environmental pollution remediation," *Applied Catalysis B: Environmental*, http://dx.doi.org/10.1016/j.apcatb.2016.05.052, 106 pgs., (2016).
Moniz et al., "Visible-light driven heterojunction photocatalysts for water splitting—a critical review," *Energy and Environmental Science*, 8: 731-759 (2015).
Muñoz-Batista et al., "Effect of exfoliation and surface deposition of $MnO_X$ species in g-$C_3N_4$: Toluene photo-degradation under UV and visible light," *Applied Catalysis B: Environmental*, 203: 663-672 (2017) (published online Oct. 17, 2016).
Niu et al., "Graphene-Like Carbon Nitride Nanosheets for Improved Photocatalytic Activities," *Adv. Funct. Mater.*, 22: 4763-4770 (2012).
Ong et al., "Graphitic Carbon Nitride (g-$C_3N_4$)-Based Photocatalysts for Artificial Photosynthesis and Environmental Remediation: Are We a Step Closer to Achieving Sustainability?," *Chem. Rev.*,116: 7159-7329 (May 20, 2016).
Ong et al., "Surface charge modification via protonation of graphitic carbon nitride (g-$C_3N_4$) for electrostatic self-assembly construction of 2D/2D reduced graphene oxide (rGO)/g-$C_3N_4$ nanostructures toward enhanced photocatalytic reduction of carbon dioxide to methane," *Nano Energy*,13: 757-770 (2015).
Ong et al., "Heterojunction engineering of graphitic carbon nitride (g-$C_3N_4$) via Pt loading with improved daylight-induced photocatalytic reduction of carbon dioxide to methane," *Dalton Trans.*, 44: 1249-1257 (2015).
Ong, "2D/2D Graphitic Carbon Nitride (g-$C_3N_4$) Heterojunction Nanocomposites for Photocatalysis: Why Does Face-to-Face Interface Matter?" *Frontiers in Materials*, 4(11): 10 pgs. (Apr. 12, 2017).
Pawar et al., "Hybrid photocatalysts using graphitic carbon nitride/cadmium sulfide/reduced graphene oxide (g-$C_3N_4$/CdS/RGO) for superior photodegradation of organic pollutants under UV and visible light," *Dalton Trans.*, DOI: 10.1039/c4dt01278j, 43(33): 12514-12527 (2014).
Pawar et al., "Room-temperature synthesis of nanoporous 1D microrods of graphitic carbon nitride (g-$C_3N_4$) with highly enhanced photocatalytic activity and stability," *Scientific Reports*, 6: 31147, 14 pgs. (Aug. 8, 2016).
Prasanna et al., "A New Synergetic Nanocomposite for Dye Degradation in Dark and Light," *Scientific Reports*, 6: 38606, 10 pgs. (Dec. 8, 2016).
Qin et al., "Improving the photocatalytic hydrogen production of Ag/g-$C_3N_4$ nanocomposites by dye-sensitization under visible light irradiation," *Nanoscale*, 8: 2249-2259 (2016) (published online Dec. 24, 2015).
Rtimi et al., "Effect of surface pretreatment of $TiO_2$ films on interfacial processes leading to bacterial inactivation in the dark and under light irradiation," *Interface Focus*, 5: 20140046, 12 pgs. (2014).
Sui et al., "Dispersed conductive polymer nanoparticles on graphitic carbon nitride for enhanced solar-driven hydrogen evolution from pure water," *Nanoscale*, 5: 9150-9155 (2013).
Sun et al., "One-step in situ calcination synthesis of g-$C_3N_4$/N-$TiO_2$ hybrids with enhanced photoactivity," *RSC Adv.*, 6: 13063-13071 (2016).
Tao et al., "Scalable exfoliation and dispersion of two-dimensional materials—an update," *Phys. Chem. Chem. Phys.*, DOI: 10.1039/c6cp06813h, 40 pgs. (2016).
Thurston et al., "Preparation and Characterization of Photoactive Antimicrobial Graphitic Carbon Nitride (g-$C_3N_4$) Films," *RSC Adv.*, 6: 42240-42248) (Nov. 16, 2016).
Tian et al., "Three-Dimensional Porous Supramolecular Architecture from Ultrathin g-$C_3N_4$ Nanosheets and Reduced Graphene Oxide: Solution Self-Assembly Construction and Application as a Highly Efficient Metal-Free Electrocatalyst for Oxygen Reduction Reaction," *ACS Appl. Mater. Interfaces*, 6(2): 1011-1017 (2014).
Tian et al., "Precursor-reforming protocol to 3D mesoporous g-$C_3N_4$ established by ultrathin self-doped nanosheets for superior hydrogen evolution," *Nano Energy*, 38: 72-81 (May 24, 2017).
Tong et al., "Three-Dimensional Porous Aerogel Constructed by g-$C_3N_4$ and Graphene Oxide Nanosheets with Excellent Visible-Light Photocatalytic Performance," *ACS Appl. Mater. Interfaces*, 7(46): 25693-25701 (2015).
Tong et al., "An efficient top-down approach for the fabrication of large-aspect-ration g-$C_3N_4$ nanosheets with enhanced photocatalytic activities," *Phys. Chem. Chem. Phys.*,17: 23532-23537 (2015).
Tong et al., "Rapid and high-yield production of g-$C_3N_4$ nanosheets via chemical exfoliation for photocatalytic $H_2$ evolution," *RSC Adv.*, 5: (88149-88153) (2015).
Walter et al., "Solar Water Splitting Cells," *Chem. Rev.*, 110: 6446-6473 (2010).
Wang et al., "Construction of g-$C_3N_4$/$Al_2O_3$ hybrids via in-situ acidification and exfoliation with enhanced photocatalytic activity," *Applied Surface Science*, 394: 340-350 (2017) (published online Oct. 18, 2016).
Wang et al., "Synthesis of g-$C_3N_4$/$TiO_2$ with enhanced photocatalytic activity for $H_2$ evolution by a simple method," *International Journal of Hydrogen Energy*, 39: 6354-6363 (2014).
Wen et al., "A review on g-$C_3N_4$-based photocatalysts," *Applied Surface Science*, 391: 72-123 (2017) (published online Jul. 9, 2016).
Xiang et al., "Preparation and Enhanced Visible-Light Photocatalytic $H_2$-Production Activity of Graphene/$C_3N_4$ Composites," *J. Phys. Chem.*, 115(15): 7355-7363 (2011).
Xing et al., "A new type of carbon nitride-based polymer composite for enhanced photocatalytic hydrogen production," *Chem. Commun.*, 50: 6762-6764 (2014).
Xu et al., "Insights into Enhanced Visible-Light Photocatalytic Hydrogen Evolution of g-$C_3N_4$ and Highly Reduced Graphene Oxide Composite: The Role of Oxygen," *Chem. Mater.*, http://dx.doi.org/10.1021/cm504265w, 27(5): 1612-1621 (Feb. 3, 2015).
Xu et al., "Light-Emitting Conjugated Polymers with Microporous Network Architecture: Interweaving Scaffold Promotes Electronic Conjugation, Facilitates Exciton Migration, and Improves Luminescence," *J. Am. Chem. Soc.*, 133: 17622-17625 (2011).

(56) References Cited

OTHER PUBLICATIONS

Xu et al., "g-$C_3N_4$ modified $TiO_2$ nanosheets with enhanced photoelectric conversion efficiency in dye-sensitized solar cells," *Journal of Power Sources*, 274: 77-84 (2015) (published online Oct. 15, 2014).

Xu et al., "Synergic Effect between Adsorption and Photocatalysis of Metal-Free g-$C_3N_4$ Derived from Different Precursors," *Plos One*, DOI: 10.1371 journal.pone.0142616, 20 pgs. (Nov. 13, 2015).

Yan et al., "Photodegradation Performance of g-$C_3N_4$ Fabricated by Directly Heating Melamine," *Langmuir*, 25(17): 10397-10401 (2009).

Yang et al., "Ammonia-induced robust photocatalytic hydrogen evolution of graphitic carbon nitride," *Nanoscale*, 7: 18887-18890 (Oct. 20, 2015).

Yang et al., "Facile fabrication of acidified g-$C_3N_4$/g-$C_3N_4$ hybrids with enhanced photocatalysis performance under visible light irradiation," *Applied Catalysis B: Environmental*, 193: 22-35 (Mar. 25, 2016).

Zhang et al., "Robust Wide Visible-Light-Responsive Photoactivity for $H_2$ Production over a Polymer/Polymer Heterojunction Photocatalyst: The Significance of Sacrificial Reagent," *ACS Sustainable Chem. Eng.*, 3: 1501-1509 (Jun. 12, 2015).

Zhang et al., "Enhancement of visible light photocatalytic activities via porous structure of g-$C_3N_4$," *Applied Catalysis B: Environmental*, 147: 229-235 (2014).

Zhang et al., "Highly active $TiO_2$/g-$C_3N_4$/G photocatalyst with extended spectral response towards selective reduction of nitrobenzene," *Applied Catalysis B: Environmental*, 203: 1-8 (2017) (published online Oct. 4, 2016).

Zhang et al., "Recent advances in dye-sensitized semiconductor systems for photocatalytic hydrogen production," *J. Mater. Chem. A*, 4: 2365-2402 (2016).

Zhang et al., "Achieving significantly enhanced visible-light photocatalytic efficiency using a polyelectrolyte: the composites of exfoliated titania nanosheets, graphene, and poly(diallyl-dimethyl-ammonium chloride)," *Nanoscale*, 7: 14002-14009 (2015).

Zhang et al., "Origin of photoactivity in graphitic carbon nitride and strategies for enhancement of photocatalytic efficiency: insights from first-principles computations," *Phys. Chem. Chem. Phys.*, 17: 6280-6288 (2015).

Zhao et al., "Graphitic carbon nitride based nanocomposites: a review," *Nanoscale*, 7: 15-37 (2015).

Zhou et al., "A Universal Method to Produce Low-Work Function Electrodes for Organic Electronics," *Science*, 336(20): 327-332 (2012).

Zhu et al., "Isoelectric point and adsorption activity of porous g-$C_3N_4$," *Applied Surface Science*, 344: 188-195 (2015).

Zhu et al., "Mechanically exfoliated g-$C_3N_4$ thin nanosheets by ball milling as high performance photocatalysts," *RSC Adv.*, 5: 56239-56243 (Jun. 19, 2015).

Zuluaga et al., "Structural band-gap tuning in g-$C_3N_4$," *Phys. Chem. Chem. Phys.*, DOI: 10.1039/b000000x, 1-7 (2014).

\* cited by examiner

ANTIMICROBIAL PHOTOREACTIVE COMPOSITION COMPRISING ORGANIC AND INORGANIC MULTIJUNCTION COMPOSITE

CROSS-REFERENCE TO RELATED APPLICATIONS

This patent application claims the benefit of U.S. Provisional Patent Application No. 62/488,438, filed Apr. 21, 2017 and U.S. Provisional Patent Application No. 62/367,981, filed Jul. 28, 2016, each of which is incorporated by reference.

BACKGROUND OF THE INVENTION

Infectious diseases kill more people worldwide each year than any other single cause. Minimizing infections caused by pathogenic microorganisms is a great concern in many fields, particularly in medical devices, drugs, hospital surfaces/furniture, dental restoration and surgery equipment, healthcare products and hygienic applications, water purification systems, air filters, textiles, food packaging and storage, industrial or domestic appliances, aeronautics, etc. Particularly in hospitals, great efforts and significant costs are incurred in the fight against infections.

Infections are produced by touching, eating, drinking, or breathing something that contains a pathogen. Generally, these infections are combated with antimicrobial agents that target the pathogen. Particularly problematic, however, are the microorganisms that can rapidly and easily mutate their genes to become resistant to these agents, making their elimination difficult. For instance, Staphylococcus aureus (S. aureus) commonly colonizes on human skin and in mucosa without causing severe problems, but if the bacteria enter the body, illnesses that range from mild to life-threatening can develop, including skin and wound infections, infected eczema, abscess infections, heart valve infections or endocarditis, pneumonia, and bloodstream infections or bacteraemia. Some S. aureus are resistant to methicillin and other β-lactam antibiotics—methicillin-resistant S. aureus (MRSA)—and require alternative types of antibiotics to treat them. Moreover, the spore-forming Clostridium difficile (C. difficile), an intestinal superbug causing symptoms ranging from diarrhea to life-threatening inflammation of the colon, is the most common bacterial infection acquired in hospitals.

Given these health hazards, considerable research effort is being devoted to creating advanced photoreactive materials that can promote, for example, processes such as the photodecomposition of organic and inorganic contaminants (Borgarello et al., Disposal of hydrogen sulfide: conventional and photochemical methods. In M. Schiavello, Ed., Photocatalysis and Environment, p. 567-581, Kluwer Academic Publishers, Dordrecht (1988); Brinkley et al., Journal of Physical Chemistry, 102, 7596-7605 (1998); Fox, Photocatalytic oxidation of organic substrates. In M. Schiavello, Ed., Photocatalysis and Environment, p. 445-467, Kluwer Academic Publishers, Dordrecht (1988); Pelizzetti et al., Photodegradation of organic pollutants in aquatic systems catalyzed by semiconductors, In M. Schiavello, Ed., Photocatalysis and Environment, p. 469-497, Kluwer Academic Publishers, Dordrecht (1988); Serpone et al., Photoreduction and photodegradation of inorganic pollutants: I. Cyanides. In M. Schiavello, Ed., Photocatalysis and Environment, p. 499-526, Kluwer Academic Publishers, Dordrecht (1988a, 1988b)), photosynthesis of organic compounds from carbon dioxide and other inorganic substrates (Anpo et al., Journal of Physical Chemistry, 101, 2632-2636 (1997); Kanemoto et al., Journal of the Chemical Society, Faraday Transactions, 92, 2401-2411 (1996)), photodecomposition of water to hydrogen and oxygen (Lauermann et al., Journal of Electroanalytical Chemistry, 228, 45-55 (1987)), and photoreduction of dinitrogen to ammonia (Augugliaro and Palmisano, Reduction of dinitrogen to ammonia in irradiated heterogeneous systems. In M. Schiavello, Ed., Photocatalysis and Environment, p. 425-444. Kluwer Academic Publishers, Dordrecht (1988)). The role of semiconducting materials as catalysts of redox reactions in natural environments and engineered systems designed to degrade hazardous chemicals is also being increasingly recognized (Schoonen et al., Journal of Geochemical Exploration, 62, 201-215 (1998); Selli et al. 1996; Stumm and Morgan 1995; Sulzberger, Photoredox reactions at hydrous metal oxide surfaces: A surface coordination chemistry approach. In W. Stumm, Ed., Aquatic Chemical Kinetics. Wiley Interscience, New York (1990)).

Despite previous efforts, there continues to be a need to provide photocatalytic composites capable of creating a light-activated antimicrobial film and various other uses.

BRIEF SUMMARY OF THE INVENTION

The invention provides a photoreactive composition comprising: (a) a photocatalytic multijunction composite comprising at least one photocatalytic heterojunction that is primarily carbon based, (b) at least one surface-coupling material, (c) optionally at least one additive selected from a charge-transfer augmenting material, a light-capturing augmenting material, an antimicrobial augmenting material(s), or a combination thereof, and (d) a carrier. The photocatalytic multijunction is photoreactive in ordinary room lighting.

Due to the antimicrobial properties of the composition, the invention also provides a method of disinfecting a surface comprising applying to the surface the photoreactive composition.

DETAILED DESCRIPTION OF THE INVENTION

Figure 1:
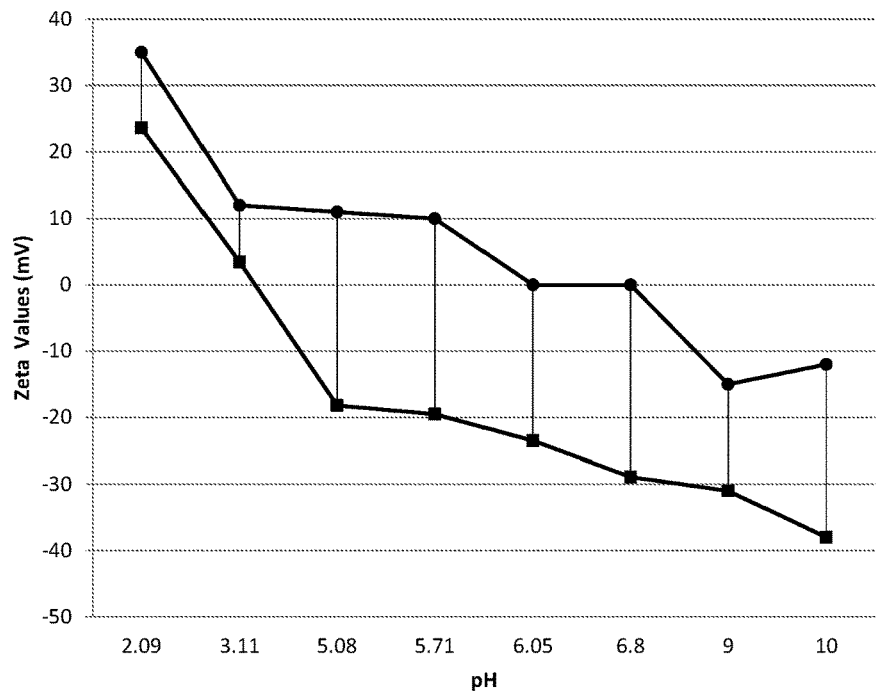
FIG. 1 illustrates zeta curves for acidified CN ("ACN") (●) and a $CN_1/CN_2$ heterojunction (■) at various pH values.

The invention is directed to a photoreactive composition, typically in the form of a dispersion, comprising a composite material that has high light-harvesting efficiency and maximizes photon utilization that can be easily applied to surfaces, e.g., using a spray or wipe, to create a light reactive antimicrobial film. The composition can be produced using low cost methods, such as oven calcination, high-energy, dry and wet milling, chemical synthesis, and sonication, all of which are easily scalable. The dispersed materials can be used in a variety of applications, such as photocatalytic and photovoltaic applications, or potentially reduced to a paste and applied to the anodes of a dye-sensitized solar cell (DSSC).

Contrary to most research aimed at developing robust photocatalytic materials, the composites of the present invention do not center on the use of transition metal oxides. The reason for this is that many metal oxides are only suitable for one half of the photocatalytic reaction. That is, metal oxides have band edges either inside or outside the potential for splitting water, and thus only provide half of the reaction. Metal oxides act either as an oxidation catalyst or a reduction catalyst, but not both. This is true for several well-investigated semiconductors, such as $TiO_2$, $Fe_2O_3$, $WO_3$, $BiVO_4$, and $ZnO$, which all have band edges that are incapable of unbiased overall water splitting. The band edge positions of these metal oxides are only suitable for one of the half reactions. See, e.g., Xu et al. (*American Mineralogist*, 2000, 85(3-4), 543-556).

In photochemical reactions, there can only be a transfer of electrons between the semiconductor and sorbed reactants (e.g., for water or toxic pollutants) if the energetic states of the semiconductor and the sorbent are at approximately the same energy level. The energy level of the energetic states of sorbates undergoing an electron transfer can be approximated by the standard redox potential ($E_0$), whereas relevant energy levels for a semiconductor are the top of the valence band ($E_V$) and the bottom of the conduction band ($E_C$). The relative energetics of $E_V$ and $E_C$ versus $E_0$ is the fundamental property that dictates whether an electron transfer between the semiconductor and sorbate is feasible.

The present invention seeks to provide photocatalytic composites that have antimicrobial properties and can be attached directly to a substrate through a coupling agent or embedded in a cationic polymer matrix. Both of these methods form a light-activated antimicrobial film that uses surface water that arises from normal atmospheric humidity as the sorbent. Accordingly, the photocatalytic composites of the present invention are designed to exceed the $E_0$ of $H_2O$, which is between −0.42 V and +0.81 V (i.e., 1.23 eV).

In addition to having antimicrobial properties, the photoreactive composition can be used to split water to create hydrogen, convert CO2 to methanol or other hydrocarbons, and/or degrade organic pollutants, such as dye in textile waste streams.

Accordingly, the invention provides a photoreactive composition comprising:

(a) a photocatalytic multijunction composite comprising at least one photocatalytic heterojunction that is primarily carbon based, (b) at least one surface-coupling material, (c) optionally at least one additive selected from a charge-transfer augmenting material, a light-capturing augmenting material, an antimicrobial augmenting material(s), or a combination thereof, and (d) a carrier, wherein the photocatalytic multijunction is photoreactive in ordinary room lighting.

The effectiveness of the photoreactive composition, described herein, is best viewed in terms of: i) its ability to "kill now" when applied to a surface as a traditional disinfectant—even without the presence of conventional germicidal chemicals that can be toxic, and ii) its ability to "kill later," i.e., to kill persistently into the future post-application. The technology is highly tunable because the "kill-later" feature stemming from the photocatalytic multijunction composite can be augmented with a "kill now" material, such as ethanol as the dispersant, and/or with the addition of one or more cationic polymers and/or one or more conventional antimicrobial agents to the composition. The composition can be further tuned to create films of various thicknesses, solvency, and/or adhesion. Alternatively, or in addition, one or more cationic polymers can be added to target specific pathogens and/or to design products with various cost profiles. These and other advantages of the invention, as well as additional inventive features, will be apparent from the description of the invention provided herein.

The photoreactive composition can harvest light at any suitable wavelength, or in any suitable range of the electromagnetic spectrum. For example, the photoreactive composition can harvest light at wavelengths greater than about 250 nm, for example, greater than about 275 nm, greater than about 300 nm, greater than about 325 nm, greater than about 350 nm, greater than about 375 nm, greater than about 400 nm, greater than about 450 nm, greater than about 500 nm, or greater than about 550 nm. Alternatively, or in addition, the photoreactive composition can harvest light at wavelengths less than about 950 nm, for example, less than about 925 nm, less than about 900 nm, less than about 875 nm, less than about 850 nm, less than about 825 nm, less than about 800 nm, less than about 750 nm, or less than about 700 nm. Thus, the composition can harvest light in a range bounded by any two of the aforementioned endpoints. For example, in some embodiments, the composition will harvest light at least over a range of about 400 nm to about 700 nm (e.g., about 350 nm to about 800 nm, about 300 nm to about 900 nm).

The photoreactive composition comprises at least one photocatalytic multijunction composite, in which each composite is the same or different. However, at least one photocatalytic multijunction composite in the composition must comprise at least one photocatalytic heterojunction that is primarily carbon based.

The photocatalytic multijunction composite can comprise any suitable number of heterojunctions. For example, the photocatalytic multijunction composite can comprise at least 1 heterojunction, at least 2 heterojunctions, at least 3 heterojunctions, at least 4 heterojunctions, at least 5 heterojunctions, at least 6 heterojunctions, at least 7 heterojunctions, at least 8 heterojunctions, or at least 9 heterojunctions. In certain embodiments, the photocatalytic multijunction composite is a blend of two or more such multijunction composites. As used herein, "blend" refers to any number of multijunction composites that are not coupled. For example, the photocatalytic multijunction composite can comprise a blend of a 4-junction composite and a 3-junction composite, a blend of a 4-junction composite and a 5-junction composite, a single 3-junction composite, a single 4-junction composite, a single 5-junction composite, a single 7-junction composite, or a single 9-junction composite. Without wishing to be bound by any particular theory, it is believed that the two multijunctions should not be coupled because they do not have band edges that will foster optimum charge transfer. As used herein, "band edges" refer to the ability of a material to transfer charge to another material. Band edges can determine the effectiveness of a photo-catalyst for chemically oxidizing or reducing a particular substance, how effective the charge transfer is between heterojunctions, and/or the impact the relative band gaps have on electron-hole recombination.

The photocatalytic multijunction composite can comprise junctions with any suitable band gap energies. Generally, the level, and number, of band gap energies will be used as a direct corollary to the wavelength, and amount, of light to be harvested, respectively. The junctions can have any band gap energy between about 0 eV and about 5 eV (e.g., about 0.2 eV and about 5 eV, about 0.2 eV and about 4 eV, about 0.2 eV and about 3.5 eV, about 0.5 eV and about 5 eV, about 0.5 eV and about 4 eV, or about 0.5 eV and about 3.5 eV). In some embodiments, a junction will have more than one band gap energy. In certain embodiments, a junction will have a graduated band gap energy. As used herein, "graduated band gap energy" refers to a range of band gap energies (e.g., 1.04 eV to 1.7 eV).

Generally, the photocatalytic multijunction composite comprises one or more organic material(s) and one or more inorganic material(s), but the composite comprises at least one photocatalytic heterojunction that is primarily organic, i.e., carbon-based. As used herein, "primarily" refers to the majority (e.g., 50% or more, 55% or more, 60% or more, 65% or more, 70% or more, 75% or more, 80% or more, 85% or more, 90% or more, 95% or more, 97% or more, 98% or more, or 99% or more) of the composition of the multijunction composite. In an embodiment, the composition comprises at least one photocatalytic heterojunction that primarily (e.g., 50% or more) comprises a carbon-based material, such as graphitic carbon nitride.

The photocatalytic multijunction composite and/or heterojunction can comprise any suitable organic, carbon-based material, such as, graphitic carbon nitride ($g\text{-}C_3N_4$), acidified carbon nitride (ACN), graphene oxide, reduced graphene oxide, a conjugated polymer, or a combination thereof. In some aspects, the conjugated polymer is poly(3-hexylthiophene) (P3HT), polypyrrole (Ppy), polycarbazole, polyindole, polyazepine, polyaniline, polyfluorene, polyphenylene, polypyrene, polyazulene, polynaphthalene, polythiophene (Ptp), poly(3,4-ethylenedioxythiophene), poly(p-phenylene sulfide), polyacetylene, poly(p-phenylene vinylene), or a combination thereof. In certain embodiments, the organic material is selected from graphitic carbon nitride ($g\text{-}C_3N_4$), acidified carbon nitride (ACN), and a combination thereof.

In certain embodiments, the organic material is graphitic carbon nitride ($g\text{-}C_3N_4$). The graphitic carbon nitride ($g\text{-}C_3N_4$) can be any combination of one or more different forms of graphitic carbon nitride (e.g., $g\text{-}C_3N_{4(700)}$ or $g\text{-}C_3N_{4(500)}$). For example, $g\text{-}C_3N_{4(700)}$ is CN calcinated at 700° C., and has a wider band gap than $g\text{-}C_3N_{4(500)}$, which is calcinated at 500° C. As a polymeric semiconductor, it is mainly composed of carbon and nitrogen, and therefore it is considered environmentally friendly. Moreover, $g\text{-}C_3N_4$ can be easily prepared from several nitrogen-containing organic compounds, including cyanamide, dicyandiamide, melamine, urea, and thiourea. Without wishing to be bound to any particular theory, the graphitic carbon nitride ($g\text{-}C_3N_4$) material has advantages that include: 1) as an organic material, it can easily be coupled, with a coupling agent (e.g., a titanate, carboxylated branched PEI) to inorganic semiconductors; 2) it is a very porous material, which makes it easily absorb nano and crystalline organic and inorganic materials as well as dye sensitizers; 3) it has a unique electronic structure; 4) it has high chemical and thermal stability and/or 5) the recombination of electron-hole pairs is reduced by forming hetero-structures with $g\text{-}C_3N_4$ and various other semiconductor materials. Generally, the graphitic carbon nitride ($g\text{-}C_3N_4$) can easily be prepared as a particle, platelet, or a rod component.

In some embodiments, a photocatalytic heterojunction with antimicrobial properties can be formed by simultaneous thermo-polymerization of urea and of thiourea, which creates two different phases that enable the formation of an isotype heterojunction at the interface of the two different phases. As used herein, "$CN_1/CN_2$" refers to a urea- and thiourea-produced heterojunction. This $CN_1/CN_2$ heterojunction comprises two different band structures, leading to the enhanced photocatalytic activity arising from promoted charge separation. The creation of such $g\text{-}C_3N_4/g\text{-}C_3N_4$ heterojunctions are described in Dong et al. (*ACS Appl. Mater. Interfaces*, 2013, 5, 11392-11401).

The $CN_1/CN_2$ material is mesoporous, which augments the specific surface area of the materials. Higher specific surface area translates to higher photocatalytic performance. An unintended consequence of formulating with urea, not seen by Dong et al. (vide supra) is that by forming the heterojunction with both urea and thiourea, the urea provided a soft bubble templating that increases the porosity of the finished product. Specifically, the urea decomposes into bubbles during the thermal polymerization process, which leads to the porous structure of $CN_1/CN_2$. This was brought to light by Zhang et al. (*Applied Catalysis B: Environmental*, 2014, 147, 229-235), in which Zhang et al. demonstrated that at a calcination temperature of 550° C. and using 70% urea, the surface area of the as-prepared $g\text{-}C_3N_4$ increased from 5.4 $m^2/g$ to 60 $m^2/g$. Even though the synthesis described herein was limited to 50% urea and the calcination temperature was 550° C., the $CN_1/CN_2$ heterojunction is considered mesoporous.

After subjecting a mixture of urea and thiourea to thermal condensation to create a mesoporous heterojunction ($CN_1/CN_2$), the performance of the heterojunction can be further improved by chemical oxidation. Oxidation increases the heterojunction's performance by introducing H and O elements into the $CN_1/CN_2$ composite, resulting in a broader optical absorption range, higher light absorption capability, and more efficient separation of photo generated electrons and holes. The oxidant was a mixture of 30/10 v/v $H_2O_2$/$NH_3$:$H_2O$ (Liao et al., *Phys. Chem. Chem. Phys.*, 2015, 17, 27826-27832).

Bulk $g\text{-}C_3N_4$ can be transformed into high surface area platelets by using a modified method reported in Tong et al. (*RSC Adv.*, 2015, 5, 88149-88153) for preparing $g\text{-}C_3N_4$ platelets. The platelets described herein were created through decanting in both $H_2O$ and methanol, not filtering, and then washed (not to neutral), but to a pH of approximately 2, giving a zeta value near +35. Conversion of bulk $g\text{-}C_3N_4$ to $g\text{-}C_3N_4$ platelets requires the use of highly concentrated sulfuric acid, such that $g\text{-}C_3N_4$ platelets described herein are referred to as acidified CN ("ACN").

Structural defects in $g\text{-}C_3N_4$ created by incomplete polymerization of $g\text{-}C_3N_4$ will reduce the photocatalytic activity of $g\text{-}C_3N_4$, but a technique that reduce these defects, such as high energy ball milling, can be used to improve the photocatalytic activity.

A multijunction composite comprising ACN platelets and a $CN_1/CN_2$ heterojunction can be formed by electrostatic coupling. The methods described herein control the pH in order to maximize the charge difference between the ACN and $CN_1/CN_2$. The optimal pH for coupling the two components for the compositions reported herein was determined by developing zeta curves for both the ACN and the $CN_1/CN_2$ heterojunction (see, for example, FIG. 1). FIG. 1 shows the optimal zeta difference between the two components is at a pH of approximately 5.5. The pH was then adjusted to an operational pH of 6.3 to account for a 90:10 (% v/v) methanol:$H_2O$ mixture (see, Measurements in Alcohol-water mixtures, using aqueous standard buffer solutions for calibration, W. J. Gelsema, et al., *Recueil*, 85, 647-660 (1966)).

The photocatalytic multijunction composite can comprise any suitable inorganic material in addition to the photocatalytic heterojunction that is primarily carbon based. For example, the photocatalytic multijunction composite can comprise a transition metal oxide, a transition metal sulfide, a transition metal selenide, an alloy comprising copper, indium, gallium, and diselenide (CIGS), or a combination thereof. In some aspects, the transition metal oxide is selected from the group consisting of silicon dioxide (including fumed silica, amorphous silica, precipitated silica, hydrophilic silica, and hydrophobic silica), titanium dioxide, zinc oxide, iron oxide, aluminum oxide, cerium oxide, zirconium oxide, and a combination thereof; the transition metal sulfide is selected from cadmium sulfide, molybdenum disulfide, tungsten sulfide, silver sulfide, zinc sulfide, selenium sulfide, iron disulfide, nickel sulfide, ruthenium sulfide, cobalt sulfide, and a combination thereof. In other aspects, the transition metal selenide is selected from cadmium selenide, copper selenide, copper geranium selenide, copper indium gallium selenide, copper titanium selenide, indium selenide, manganese diselenide, titanium selenide, tungsten diselenide, silver selenide, disilver selenide, digold, triselenide, zinc sulfide, iron selenide, nickel selenide, ruthenium selenide, cobalt selenide, and a combination thereof. In certain embodiments, the inorganic material is selected from cadmium sulfide (CdS), cadmium selenide (CdSe), an alloy comprising copper, indium, gallium, and diselenide (CIGS), and a combination thereof.

In certain embodiments, the inorganic material is selected from cadmium sulfide (CdS), cadmium selenide (CdSe), an alloy comprising copper, indium, gallium, and diselenide (CIGS), and combinations thereof. Generally, cadium sulfide (CdS) has a band gap of 2.4 eV, cadmium selenide (CdSe) has a band gap of 1.7 eV, and CIGS has a graduated band gap ranging from about 1.7 eV to about 1.04 eV. Thus, CIGS is a highly tunable material (i.e., the band gap is determined by the relative abundance of its four components) which makes it capable of harvesting the light spectrum from 625 nm to about 700 nm. An object of the invention is to minimize the use of metal oxides that only provide half chemical reactions. In general, though, the photocatalytic composites described herein do not rely on the primary use of metal oxides yet provide exceedingly high oxidative and reducing power.

In some embodiments, the photoreactive multijunction composite is comprised of platelets, micro-particles, nanoparticles, crystalline colloidal materials, or a combination thereof that has high light-harvesting efficiency and maximizes photon utilization. As used herein, the term "particle" includes sphere-like particles (e.g., spheres) and other shapes, such as platelets, rods, cubes, and flakes or combinations of various shapes and morphologies. Either low-level room lighting or broad-spectrum outdoor light can be harvested based upon the specific composition. In some embodiments, the photocatalytic multijunction composite comprises one or more crystalline component(s), one or more platelet component(s), one or more nano rod component(s), one or more mesoporous components(s), or a combination thereof. In some embodiments, the one or more crystalline component(s), one or more a platelet component(s), one or more nano rod component(s), and/or one or more mesoporous components(s) are sub-micron particles (i.e., have an effective diameter less than one millionth of a meter, including an effective diameter less than one billionth of a meter). In some embodiments, the one or more crystalline component(s), one or more a platelet component(s), one or more nano rod component(s), and/or one or more mesoporous components(s) stand alone in the photocatalytic multijunction composite. In any of the foregoing embodiments, the components of the composition combine to form colloids or agglomerates.

In some instances, the photocatalytic multijunction composite comprises one or more crystalline component(s). As used herein, "crystalline" refers to any solid structure with highly ordered constituents (e.g., atoms, molecules, and/or ions). The crystalline component can be crystalline, polycrystalline, quasicrystalline, or amorphous. The crystalline component can have any suitable crystal lattice structure. For example, the crystal lattice can be triclinic, monoclinic, orthorhombic, tetragonal, hexagonal, or cubic.

In some instances, the photocatalytic multijunction composite comprises one or more platelet component(s). As used herein, "platelet" refers to one or more structural sheet(s) of a material (e.g., graphitic carbon nitride, ACN, graphene oxide, or reduced graphene oxide) that have been stacked. Generally, the platelets have a thickness, as measured orthogonal to the stacking plane, of less than about 1 um (e.g., less than about 100 nm, less than about 10 nm, or less than about 1 nm).

In some instances, the photocatalytic multijunction composite comprises one or more nano rod component(s). As used herein, "nano rod" refers to a rod-like structure of a material (e.g., graphitic carbon nitride, ACN, graphene oxide, or reduced graphene oxide). Generally, the nano rods have a rod-like structure wherein all dimensions are less than about 1 μm (e.g., less than about 100 nm, less than about 10 nm, or less than about 1 nm).

In some instances, the photocatalytic multijunction composite comprises one or more mesoporous components(s). As used herein, "mesoporous" refers to a porous material (e.g., graphitic carbon nitride, ACN, graphene oxide, or reduced graphene oxide), wherein the material contains pores from about 2 nm to about 50 nm (e.g., from about 5 nm to about 50 nm, about 10 nm to about 50 nm, from about 20 nm to about 50 nm, from about 25 nm to about 50 nm, from about 2 nm to about 40 nm, from about 2 nm to about 30 nm, from about 2 nm to about 25 nm, or from about 5 nm to about 25 nm).

In some instances, the inorganic materials, organic materials, and/or photocatalytic multijunction composite(s) are milled prior to use via any suitable technique (e.g., wet milling, dry milling). As used herein, "milling" refers to any grinding, crushing, and/or cutting. In certain embodiments, the inorganic materials, organic materials, and/or photocatalytic multijunction composite(s) are wet milled using very high revolutions per minute (RPM), i.e., high-energy milling, which creates nano (<100 nm) and crystalline (<10 nm) materials.

Figure 2:
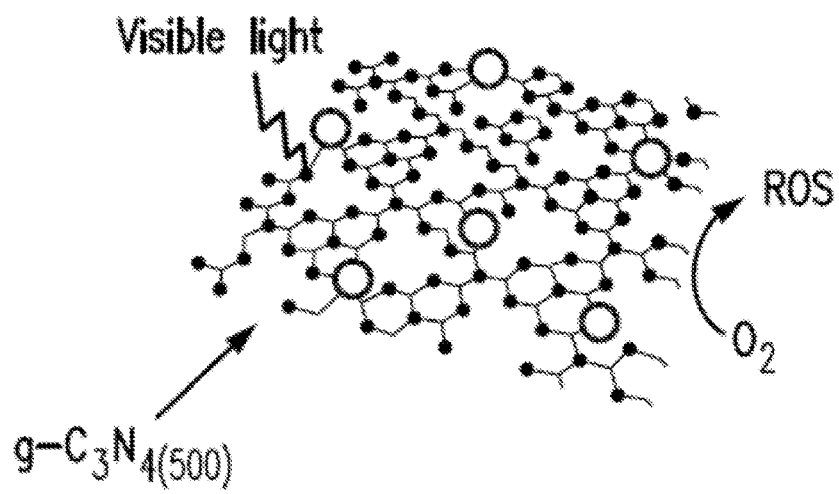
FIG. 2 illustrates a $g-C_3N_4$ matrix containing dispersed semi-conductor metals.

In a specific example, to form a photocatalytic multijunction composite, the inorganic materials are first nanoized and crystallized by exposing them, in powder form, to high speed milling in a planetary ball mill. These prepared inorganic materials are then mixed with powdered $g-C_3N_4$ components and then calcinated to create graphene-like polymers that contain dispersed and coupled semi-conductor metals. The finished product is illustrated in FIG. 2. Following calcination, the material is hand ground and then wet milled for 1 to 4 hours to create nano and crystalline materials. The wet milling also makes it possible to capture, and maintain in the dispersion, numerous unseen nano and crystalline particles that were not initially alloyed or coupled to the g-$C_3N_4$. Without wishing to be bound by any theory, it is believed that the presence of these crystalline nano particles contributes greatly to the photoreactive composition's ability to efficiently harvest light. Firstly, the mixed morphology of the compositions, consisting of micro (>100 nm) and nano (≤100 nm) platelets as well as crystalline-like particles, fosters light diffraction, which in turn reduces the loss of photons. Secondly, the nano crystalline particles have an exceedingly high surface area, which means there is more surface to be photoreactive. Thus, retaining the particles results in a system that is more photoreactive because a greater number of photons are captured and they are used more efficiently.

In certain embodiments, the organic and inorganic materials in the multijunction composite are tightly (strongly) coupled but not covalently bound to one another. Without wishing to be bound to any particular theory, a strong interfacial bond is necessary to assure maximum charge transfer between the constituents of the multijunction composite. When materials in a multijunction are tightly coupled, these materials synergistically harvest distinct contiguous slices of the indoor light spectrum. Tight coupling is important because the quality of the interface between the materials can affect the performance of the multijunction material.

In some embodiments, the photoreactive composition further comprises heterojunction particles. As used herein, "heterojunction particles" refer to any inorganic materials (e.g., CdS, CdSe, and CIGS) and/or organic materials that do not manage to couple to form a multijunction composite during the milling process, but instead couple (e.g., alloy) with one another. In certain embodiments, platelets of g-$C_3N_4$, such as g-$C_3N_{4(500)}$ and g-$C_3N_{4(700)}$, also act as heterojunction particles. In some instances, free nano and/or crystalline particles can agglomerate and act as a heterojunction particles due to interfacial-charge transfers that can occur within the particles of the agglomerate.

In some embodiments, the photocatalytic multijunction composite has one or more valence band(s) below the oxidation potential needed for splitting water. In certain embodiments in which the composite has one or more valence band(s) below the oxidation potential needed for splitting water, the photocatalytic multijunction composite can photocatalytically oxidize water to form hydroxy radicals.

In other embodiments, the photocatalytic multijunction composite has one or more conduction band(s) (CBs) above the reduction potential needed for splitting water. In certain of these embodiments, the photocatalytic multijunction composite can photocatalytically reduce water to form superoxide anions.

Alternatively, the photocatalytic multijunction composite can have one or more valence band(s) (VBs) below the oxidation potential needed for splitting water and one or more conduction band(s) above the reduction potential needed for splitting water.

Without wishing to be bound by any particular theory, in order to photocatalytically accelerate the reduction or oxidation of a chemical, the conduction band and/or valence band must be above the energy levels of the chemical being oxidized or reduced. For example, for photocatalytic water splitting, ideally the conduction band position should be more negative than the reduction potential of $H^+/H_2$ (which is −0.42 eV as measured relative to the normal hydrogen electrode (NHE) potential, at pH 7), whereas the valence band position should be more positive than the oxidation potential of $O_2/H_2O$ (which is +0.81 eV as measured relative to the normal hydrogen electrode (NHE) potential, at pH 7). Taken together, the band gap energy of a catalyst that is capable of splitting water (through both oxidation and reduction) should therefore be greater than 1.23 eV (i.e., the difference between +0.81 eV and −0.42 eV). The band gap energy has implications for light harvesting. For example, if the goal is to split water using the full light spectrum, materials with a band gap of less than 1.23 eV, i.e., those materials that harvest light in the near-infrared and infrared part of the spectrum—will either have a CB that is more negative than −0.42 V or a VB that is less positive than +0.81, but not both. Thus, lower band gap materials will either split water through oxidation or reduction but not both.

In some embodiments, the photocatalytic multijunction composite has one or more conduction band(s) more negative than about −0.42 eV at pH 7. For example, the photocatalytic multijunction composite has one or more conduction band(s) more negative than about −0.45 eV (e.g., more negative than about −0.50 eV, more negative than about −0.55 eV, more negative than about −0.60 eV, more negative than about −0.70 eV, more negative than about −0.80 eV, more negative than about −0.90 eV, or more negative than about −1.0 eV).

In some embodiments, the photocatalytic multijunction composite has one or more valence band(s) more positive than about +0.81 eV at pH 7. For example, the photocatalytic multijunction composite has one or more valence band(s) more positive than about +0.85 eV (e.g., more positive than about +0.90 eV, more positive than about +0.95 eV, more positive than about +1.0 eV, more positive than about +1.1 eV, or more positive than about +1.2 eV). In certain embodiments, the multijunction composite has one or more conduction band(s) more negative than about −0.42 eV at pH 7 and one or more valence band(s) more positive than about +0.81 eV at pH 7. Thus, in certain embodiments, the photocatalytic multijunction composite has a band gap energy greater than about 1.23 eV.

In some embodiments, the photocatalytic multijunction composite comprises one or more organic material(s) and one or more inorganic material(s), such that there is more than one valence band, wherein the charge transfer from one valence band to the next valence band is uphill. For example, the charge transfer will proceed from more positive band energies to less positive band energies as the charge transfers from one valence band to the next. In some embodiments, the photocatalytic multijunction composite comprises one or more organic material(s) and one or more inorganic material(s), such that there is more than one conduction band, wherein the charge transfer from one conduction band to the next conduction band is downhill. For example, the charge transfer will proceed from more negative band energies to less negative band energies as the charge transfers from one conduction band to the next. In some embodiments, the photocatalytic multijunction composite comprises one or more organic material(s) and one or more inorganic material(s), such that there is more than one valence band, wherein (i) the charge transfer from one valence band to the next valence band is uphill, and there is more than one conduction band, and (ii) the charge transfer from one conduction band to the next conduction band is downhill.

It is an objective of the present invention to provide advanced photocatalytic materials with highly effective inter-particle and interfacial charge transfers. This is achieved by sequencing the assembly of appropriately selected organic and inorganic photocatalytic materials to create a strongly coupled multijunction composite that minimizes the recombination of electron and holes. As far as possible, the band edges of each adjacent material should have a potential that encourages the flow of electrons and holes. This is achieved when the electron flow at the CB edges is from higher to lower negative potentials (negatively charged electrons move to a lower negative potential, i.e., more positive). At the bottom of the band gap, the positive charges of the holes migrate from a higher to a lower potential. In other words, they form an energy level cascade that is more conducive to charge transport inside the multijunction and reduces the recombination of electron holes, thus improving the photocurrent and ultimately improving the efficiency of the multijunction.

The photoreactive composition can comprise any suitable amount of the photocatalytic multijunction composite and surface-coupling material to form a residual self-sanitizing film. The photoreactive composition can comprise, for example, the photocatalytic multijunction composite in an amount of at least 0.1 wt % based on the total components of the photoreactive composition ("bac") (e.g., at least 0.2 wt % bac, at least 0.3 wt % bac, at least 0.4 wt % bac, at least 0.5 wt % bac, at least 1 wt % bac, at least 2 wt % bac, or at least 5 wt % bac). Alternatively, or in addition, the photoreactive composition can comprise the photocatalytic multijunction composite in an amount of 25 wt % bac or less (e.g., 20 wt % bac or less, 15 wt % bac or less, 10 wt % bac or less, 9 wt % bac or less, 8 wt % bac or less, 7 wt % bac or less, 6 wt % bac or less, or 5 wt % bac or less). Thus, the photoreactive composition can comprise the photocatalytic multijunction composite in an amount bounded by any two of the aforementioned endpoints.

The photoreactive composition preferably also comprises at least one surface-coupling material that allows the composition to adhere to the surface of a substrate to form a residual self-sanitizing film that cannot be immediately washed away. The surface-coupling material typically has an attractive force to a surface to be coupled to, the photocatalytic multijunction composite, or both. Suitable examples of a surface-coupling material include a titanate, a silane, a carboxylated branched polyethylenimine (PEI)-based polymer, a carboxylated linear PEI-based polymer, a polyethylenimine (PEI)-based polymer, cationic block copolymers, and other polymers that will create "sticky," reactive groups, such as acyl or carboxylic acid, and carboxylic acid derivatives, salts of any of the foregoing, and a combination thereof. Preferably, the surface-coupling material is a carboxylated branched PEI-based polymer, as it does not detract from the cationic charge of the polymers. In some embodiments, the surface coupling material is a low-work function material. As used herein, "low-work function material" refers to a material that reduces the resistance to charge transfer from the photocatalytic multijunction composite to the air moisture.

In some embodiments, the surface-coupling material is a titanate. The titanate can be any suitable titanate that increases the composition's ability to adhere to a surface. Typically, the titanate is selected from an alkoxy titanate, a neoalkoxytitanate, an oxyacetate chelated titanate, an ethylene chelated titanate, a pyrophosphate titanate, and a combination thereof. In preferred embodiments, the titanate is selected from titanium IV 2,2(bis 2-propenolatomethyl)butanolato, tris neodecanoato-O, titanium IV 2,2(bis 2-propenolatomethyl)butanolato, tris(dodecyl)benzenesulfonato-O, titanium IV 2,2(bis 2-propenolatomethyl)butanolato, tris(dioctyl)phosphato-O, titanium IV 2,2(bis 2-propenolatomethyl)butanolato, tris(dioctyl)pyrophosphato-O, titanium IV 2,2(bis 2-propenolatomethyl)butanolato, tris(2-ethylenediamino)ethylato, titanium IV 2,2(bis 2-propenolatomethyl)butanolato, tris(3-amino)phenylato, titanium IV 2,2(bis 2-propenolatomethyl)butanolato, tris(6-hydroxy)hexanoato-O, or a combination thereof. Typically, the titantate is titanium IV 2,2(bis 2-propenolatomethyl)butanolato, tris neodecanoato-O.

The photoreactive composition can comprise any suitable amount of titanate to form a residual self-sanitizing film. The photoreactive composition can comprise, for example, titanate in an amount of 0.1 wt % bac or more (e.g., 0.2 wt % bac or more, 0.3 wt % bac or more, 0.4 wt % bac or more, or 0.5 wt % bac or more). Alternatively, or in addition, the photoreactive composition can comprise titanate in an amount of 6 wt % bac or less (e.g., 5 wt % bac or less, 4 wt % bac or less, 3 wt % bac or less, 2 wt % bac or less, 1 wt % bac or less, 0.9 wt % bac or less, 0.8 wt % bac or less, or 0.7 wt % bac or less). Thus, the photoreactive composition can comprise titanate in an amount bounded by any two of the aforementioned endpoints.

In some embodiments, the surface-coupling material is a carboxylated PEI-based polymer ("PEI—COOH") that is either branched, linear, or a mixture of branched and linear. In certain embodiments, the surface-coupling material is a carboxylated branched polyethylenimine-based polymer. The PEI—COOH can be purchased commercially or prepared from PEI. For example, bromoacetic acid in water can be added to PEI in water. The resulting mixture is stirred and then filtered to isolate the polymer and remove unreacted acid. The PEI—COOH can have any suitable molecular weight but typically has a number average molecular weight between 15,000 g/mol and 250,000 g/mol. The PEI—COOH can be used in a suitable amount that usually ranges from 0.001 wt % bac to 3 wt % bac, including ranges with end points at 0.01 wt % bac, 0.1 wt % bac, 0.5 wt % bac, 1 wt % bac, 1.5 wt % bac, 2 wt % bac, and/or 2.5 wt % bac. A preferred amount ranges from 0.001 wt % bac to 0.01 wt % bac, such as 0.001 wt % bac.

In some embodiments, the surface-coupling material is a silane compound. In general, a silane coupling agent has functional groups at both terminal ends that allow an organic material, such as the primarily carbon-based multijunction composite, to bond to an inorganic group, such as a substrate. The silane compound can have the formula R—$(CH_2)_n$—Si—$X_3$, in which R is an organofunctional group (e.g., optionally substituted linear or branched $C_1$-$C_{20}$ alkyl, optionally substituted aryl, such as phenyl or naphthyl, amino, such as —$NH(CH_2)_3NH_2$, epoxy, or methacryloxy), n is an integer from 0 to 6, and X is a hydrolyzable group (e.g., alkoxy, acyloxy, halo, or amino). Suitable examples include a trialkoxysilane and a monoalkoxysilane, in which the alkoxy is $C_1$-$C_6$ alkoxy (e.g., methoxy, ethoxy, propoxy, isopropoxy, butoxy, or a combination thereof), a dipodal (branched) silane with two alkoxy-silane branches, a cyclic azasilane, a vinyl silane, an acryloxy silane, an epoxysilane, and an aminosilane, or any combination thereof. Specific examples of silane compounds include methyltrimethoxysilane, methyltriethoxysilane, isobutyltrimethoxysilane, n-octytriethoxysilane, phenyltrimethoxysilane, vinyltrichlorosilane, vinyltris(β-methoxyethoxy)silane, vinyltriethoxysilane, vinyltrimethoxysilane, 3-metacryloxypropyl-trimethoxysilane, β-(3,4-epoxycyclohexyl)-ethyltrimethoxysilane, γ-glycidoxypropyl-trimethoxysilane, γ-glycidopropyl-methylidiethoxysilane, N-β(aminoethyl)-γ-aminopropyl-trimethoxysilane, N-β(aminoethyl)-γ-aminopropyl-methyldimethoxysilane, 3-aminopropyl-triethoxysilane, and N-phenyl-γ-aminopropyl-trimethoxysilane, or a combination thereof.

The photoreactive composition can comprise any suitable amount of silane coupling agent to form a residual self-sanitizing film. The photoreactive composition can comprise, for example, silane coupling agent in an amount of 0.1 wt % bac or more (e.g., 0.2 wt % bac or more, 0.3 wt % bac or more, 0.4 wt % bac or more, or 0.5 wt % bac or more). Alternatively, or in addition, the photoreactive composition can comprise silane coupling agent in an amount of 6% wt % bac or less (e.g., 5 wt % bac or less, 4 wt % bac or less, 3 wt % bac or less, 2 wt % bac or less, 1 wt % bac or less, 0.9 wt % bac or less, 0.8 wt % bac or less, or 0.7 wt % bac or less). Thus, the photoreactive composition can comprise a silane coupling agent in an amount bounded by any two of the aforementioned endpoints.

The surface-coupling material can be a cationic block copolymer, such as a high molecular weight polyethylene-based copolymer with basic or acidic adhesive groups, such as an amino and/or hydroxy. Commercial products of this type include BYK™ 4500, BYK™ 4510, BYK™ 4509, BYK™ 4512, and BYK™ 4513, which are available from BYK Chemie GmbH (Wesel, Germany). Suitable amounts of the block copolymer range from 0.001 wt % bac to 5 wt % bac, including ranges with end points at 0.01 wt % bac, 0.1 wt % bac, 0.5 wt % bac, 1 wt % bac, 1.5 wt % bac, 2 wt % bac, 2.5 wt % bac, 3 wt % bac, 3.5 wt % bac, 4 wt % bac, or 5 wt % bac. A preferred amount ranges from 0.5 wt % bac to 2 wt % bac, such as 1 wt % bac.

The surface-coupling material can also be a polymer that either naturally has or has been modified to have "sticky," reactive groups, such as an acyl group, a carboxylic acid, a carboxylic acid derivative, a sulfur-containing moiety (e.g., thio), an amino group, hydroxyl, and/or a halo-containing group. The polymer itself is any suitable moiety, preferably without a charge, such as polyethylene, polypropylene, poly(ethylene-vinylacetate), polyester, polyurethane, polyamide, polyvinyl acetate, polyvinyl alcohol, polyvinyl butyral, polyvinyl chloride, polyvinyl ether, or a combination thereof. Suitable amounts of the polymer range from 0.001 wt % bac to 3 wt % bac, including ranges with end points at 0.01 wt % bac, 0.1 wt % bac, 0.5 wt % bac, 1 wt % bac, 1.5 wt % bac, 2 wt % bac, and/or 2.5 wt % bac. A preferred amount ranges from 0.5 wt % bac to 2%, such as 1 wt % bac.

In some embodiments, the photoreactive composition further comprises at least one additive selected from a charge-transfer augmenting material, a light-capturing augmenting material, an antimicrobial augmenting material, or a combination thereof to improve the function of the photoreactive composition and/or the photocatalytic multijunction composite. For example, the charge-transfer augmenting material can enhance the charge transfer from the photocatalytic multijunction composite(s) to ambient moisture, enhance the photocatalytic performance of the photocatalytic multijunction composite(s), enhance the antimicrobial performance of the photocatalytic multijunction composite(s), or a combination thereof.

The additive can be present in any suitable location of the photoreactive composition. For example, the additive can be dispersed on the outer edge of the photocatalytic multijunction composite, on the surface of the photocatalytic multijunction composite (i.e., attached to the surface such that the additive is a pendant substituent), in the carrier, or a combination thereof. As used herein, "outer edge" refers to a barrier within the multijunction composite such that the barrier separates the bulk material within the multijunction composite from the air moisture surrounding the multijunction composite. Generally, the charge-transfer augmenting material is positioned to enhance internal interfacial charge transfer, i.e., within the catalyst, as well as external charge transfer between the catalyst and air moisture at the outside edge of the catalyst. Embedding the photocatalyst in most polymers would potentially mask and thus retard this external charge transfer. There are, however, a few polymers, that can safeguard against this blockage (e.g., linear or branched polyethylenimine (PEI)).

In certain embodiments, the antimicrobial augmenting material capable of enhancing the charge transfer from the photocatalytic multijunction composite to ambient moisture is a noble metal, a conjugated polymer, a low-work function material, such as polyethylenimine (PEI), or a combination thereof.

The noble metal can be any suitable noble metal, such as ruthenium, rhodium, palladium, silver, osmium, iridium, platinum, gold, and combinations thereof. In certain embodiments, the noble metal is platinum.

The conjugated polymer can be, for example, poly(3-hexylthiophene) ("P3HT"), polypyrrole ("Ppy"), polycarbazole, polyindole, polyazepine, polyaniline, polyfluorene, polyphenylene, polypyrene, polyazulene, polynaphthalene, polythiophene ("Ptp"), poly(3,4-ethylenedioxythiophene), poly(p-phenylene sulfide), polyacetylene, poly(p-phenylene vinylene), and combinations thereof. In certain embodiments, the conjugated polymer is poly(3-hexylthiophene) ("P3HT").

In some embodiments, the light-capturing augmenting material can enhance the photocatalytic performance of the photocatalytic multijunction composite, relative to the same antimicrobial photoreactive composition that lacks a light-capturing augmenting material. In certain embodiments, the antimicrobial augmenting material capable of enhancing the photocatalytic performance of the photocatalytic multijunction composite is a dye molecule. Suitable dyes include fluorescein, fluorescein isothiocyanate, a cyanine, a merocyanine, a hemicyanine, a perylene, a xanthene, a porphyrin (e.g., tetraphenylporphyrin), a phthalocyanine (e.g., copper phthalocyanine), a polyene, a polythiophene, a coumarin (e.g., NKX-2677, NKX-2587, NKX-2697, NKX-2753, NKX-2586, or NKX-2311), and a ruthenium-based dye (e.g., $(Bu_4N)_2[Ru(dcbpyH)_2(NCS)_2]$ (N719), $(Bu_4N)_2[Ru(dcbpy)_2(NCS)_2]$, cis-di(thiocyanato)bis(2,2'-bipyridyl-4,4'-dicarboxylate) ruthenium(II) (N3), tri(thiocyanato)-2,2',2''-terpyridyl-4,4',4''-tricarboxylate)ruthenium(II) (black dye), K8, K9, K19, and Z907), and combinations thereof. In certain embodiments, the dye molecule is fluorescein.

In some embodiments, the antimicrobial augmenting material can enhance the antimicrobial performance of the photocatalytic multijunction composite, relative to the same composition that lacks an antimicrobial augmenting material. In certain embodiments, the antimicrobial augmenting material is a cationic polymer. The cationic polymer can be any suitable cationic polymer, such as a polydiallyldialkylamine-based polymer, an acryloxyalkyltrialkylamine-based polymer, a vinylphenalkyltrialkylamine-based polymer, an acrylamidoalkyltrialkylamine-based polymer, a polyethylenimine-based polymer, and combinations thereof. In certain embodiments, the cationic polymer is a linear polyethylenimine-based polymer, polydiallyldimethylammonium chloride ("polyDADMAC") or poly(acrylamide-co-diallyldimethylammonium chloride).

In an embodiment, the cationic polymer is a polydiallyldialkylammonium-based polymer, such as a polydiallyldialkylammonium halide (e.g., a halide or halide-containing anion), a polydiallyldialkylammonium sulfate, or polydiallyldialkylammonium phosphate. In the polydiallyldialkylammonium halide, the halide can be any suitable compound in which the anion is a halide or includes a halide (e.g., bis(triflouromethane)sulfonimide, trifluoroacetate), such as, polydiallyldimethylammonium fluoride, polydiallyldimethylammonium chloride, polydiallyldimethylammonium bromide, polydiallyldimethylammonium iodide, polydiallyldimethylammonium bis(triflouromethane)sulfonimide or a combination thereof. In preferred embodiments, the polydiallyldimethylammonium halide is polydiallyldimethylammonium fluoride, polydiallyldimethylammonium chloride (polyDADMAC), or a mixture of polydiallyldimethylammonium chloride and polydiallyldimethylammonium fluoride and/or polydiallyldimethylammonium bis(triflouromethane)sulfonimide.

Preferred polydiallyldialkylammonium-based polymers are those polymers made from polymerization of diallyldialkylammonium compounds, which can be represented by the following formula:

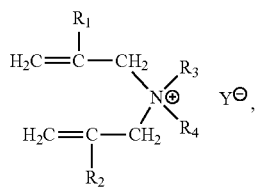

in which $R_1$ and $R_2$ are the same or different and each is hydrogen or $C_1$-$C_6$ alkyl; $R_3$ and $R_4$ are, independently, hydrogen or an alkyl, hydroxyalkyl, carboxyalkyl, carboxyamidalkyl or alkoxyalkyl group with 1 to 12 carbon atoms; and $Y^-$ represents an anion such as a halide, a halide-containing anion (e.g., bis(triflouromethane)sulfonimide), a sulfate, or a phosphate. Examples of the preferred diallydialkylammonium monomer include diallyldimethylammonium chloride (DADMAC), diallyldimethylammonium fluoride, diallyldimethylammonium bis(triflouromethane)sulfonimide, diallyldimethylammonium bromide, diallyldimethylammonium sulfate, diallyldimethylammonium phosphate, dimethyallyldimethylammonium chloride, dimethyallyldimethylammonium fluoride, dimethyallyldimethylammonium bis(triflouromethane)sulfonimide, diethylallyldimethylammonium chloride, diethylallyldimethylammonium fluoride, diethylallyldimethylammonium bis(triflouromethane)sulfonimide, diallyldi(beta-hydroxyethyl)ammonium chloride, diallyldi(beta-hydroxyethyl)ammonium fluoride, diallyldi(beta-hydroxyethyl)ammonium bis(triflouromethane)sulfonimide, diallyldi(beta-ethoxyethyl)ammonium chloride, diallyldi(beta-ethoxyethyl)ammonium fluoride, diallyldi(beta-ethoxyethyl)ammonium bis(triflouromethane)sulfonimide, diallyldiethylammonium chloride, diallyldiethylammonium fluoride, and diallyldiethylammonium bis(triflouromethane)sulfonimide. In a preferred embodiment, the cationic polymer is polyDADMAC.

In another embodiment, the cationic polymer is a polyethylenimine-based polymer, which typically is effective against non-enveloped viruses. The polyethylenimine-based polymer can be any suitable polyethylenimine-based polymer that is linear or non-linear, preferably linear. In some embodiments, the polyethylenimine-based polymer is non-chemically modified PEI, poly(ethylenimine) ethoxylated ("PETE"), a deacylated PEI, or a quaternized N-alkyl-N-methylpolyethylenimine. As used herein, "quaternized-N-alkyl-N-methylpolyethylenimine" refers to a polyethylenimine that has been partially (at least 10%, at least 20%, at least 30%, at least 40%, at least 50%, at least 60%, at least 70%, at least 80%, or at least 90%) or fully (about 98-100%) hydrolyzed, methylated, then quaternized with an alkyl substituent. The alkyl substituent in this embodiment can be any suitable alkyl sub stituent that is straight chain or branched. Generally, the alkyl substituent has a chain length chosen to be most effective against viruses, e.g., $C_{1-18}$, including $C_{8-14}$ and $C_{10-12}$. In an embodiment, the alkyl substituent is decane, dodecane, or hexadecane. In some embodiments, the polyethylenimine-based polymer is linear PEI that has not been chemically or structurally modified (e.g., does not include alkyl and/or quaternary ammonium groups).

The cationic polymer preferably has a number average molecular weight between 25,000 g/mol and 20,000,000 g/mol (e.g., 20,000,000 g/mol or less, 15,000,000 g/mol or less, 10,000,000 g/mol or less, 5,000,000 g/mol or less, or 1,000,000 g/mol or less). Alternatively, or in addition, the cationic polymer has a number average molecular weight of 25,000 g/mol or more (e.g., 50,000 g/mol or more, 100,000 g/mol or more, 150,000 g/mol or more, 200,000 g/mol or more, 250,000 g/mol or more, 300,000 g/mol or more, 350,000 g/mol or more, 400,000 g/mol or more, 450,000 g/mol or more, 500,000 g/mol or more, 550,000 g/mol or more, 600,000 g/mol or more, 650,000 g/mol or more, 700,000 g/mol or more, 750,000 g/mol or more, or 800,000 g/mol or more). Thus, the cationic polymer can have a number average molecular weight bounded by any two of the aforementioned endpoints.

The cationic polymer may or may not be used in concert with an anionic polymer to form a polyelectrolyte complex (PEC). As used herein, PEC refers to the complex that forms automatically upon addition of one or more cationic polymers in concert with one or more anionic polymers. In some embodiments, the composition does not comprise an anionic polymer. For example, when the cationic polymer is a polydiallyldialkylammonium-based polymer (e.g., a polydiallyldialkylammonium halide), the formation of a PEC is optional, i.e., an anionic polymer is optional.

When an anionic polymer is used to form a PEC, the anionic polymer preferably is a polyacrylic acid salt (PAAS). Specific examples of PAAS include polyacrylic acid alkali metal salts (e.g., polyacrylic acid sodium salt) and polyacrylic acid ammonium salts. The polyacrylic acid salt has a number average molecular weight of at least 10,000 g/mol (e.g., 20,000 g/mol or more, 40,000 g/mol or more, 60,000 g/mol or more, 80,000 g/mol or more, 100,000 g/mol or more, 120,000 g/mol or more, or 140,000 g/mol or more).

The size and internal structure of the PEC particles are regulated by, for example, the formation process, media and structural parameters, particular mixing order, mixing ratio, PEC concentration, pH, and molecular weight. Controlling the size of the PEC particle is important because the particle size affects 1) the overall stability of the Pickering PEC; 2) the solvency of the film formed by the dispersion; and 3) the adhesive strength of the film to a substrate. The solvency and adhesiveness of the film can be tuned by controlling the size of the final PEC colloidal. Some applications might require a less soluble and more adhesive film. However, tuning these two attributes will always be constrained by the stability issue. If too much anionic polymer is used, the PEC colloidal will become too large and precipitate out.

It is an aspect of the present invention that the PECs are assembled in such a way that the PECs have an average aggregate size in solution of less than about 500 nm (e.g., less than 400 nm, less than 300 nm, less than 200 nm). In some embodiments, the aggregate size is less than about 100 nm (e.g., less than 80 nm, less than 50 nm, less than 25 nm, less than 10 nm) in diameter. The particle size and molecular weights of the associative PECs can be measured via static or dynamic light scattering.

The photoreactive composition comprises a carrier. The carrier can be any suitable carrier that evaporates once the composition is applied to a desired surface, and enables the dispersion of the photoreactive composition. In some embodiments, the carrier is an organic solvent (e.g., an alcohol, acetone, dichloromethane, or dimethylformamide), water, or a combination thereof. In some embodiments, the carrier is an alcohol, water, or a combination thereof. In certain embodiments, the carrier comprises a combination of water and alcohol. A suitable alcohol includes methanol, ethanol, n-propanol, iso-propanol, n-butanol, sec-butanol, and t-butanol, or a combination thereof. In preferred embodiments, the carrier comprises ethanol (e.g., the carrier is a combination of ethanol and water). When a combination of alcohol and water is used as the carrier, the ratio of alcohol:water preferably ranges from 10:90 to 99:1 (e.g., 10:90, 20:80, 30:70, 40:60, 50:50, 60:40, 70:30, 80:20, 90:10, 95:5, and 99:1). In certain embodiments, the alcohol:water ratio ranges from 70:30 to 80:20.

In some embodiments, the photocatalytic multijunction composite is filtered prior to addition to the carrier. The photocatalytic multijunction composite can be filtered by any suitable means. For example, the photocatalytic multijunction composite can be filtered using ultrafiltration, nanofiltration, reverse osmosis filtration, or a combination thereof. In certain embodiments, the photocatalytic multijunction composite is filtered using a filter with pore size from about 0.0001 μm to about 1 μm (e.g., about 0.001 μm to about 1 μm, about 0.01 μm to about 1 μm, about 0.1 μm to about 1 μm, about 0.0001 μm to about 0.1 μm, about 0.0001 μm to about 0.001 μm, about 0.001 μm to about 0.01 μm, or about 0.01 μm to about 0.1 μm).

In some embodiments, the photocatalytic multijunction composite, at least one surface-coupling material, and carrier can be used to create a light activated film. In some instances, the photocatalytic multijunction composite and surface-coupling material can be dispersed in a miscible blend of cationic polymers (e.g., linear PEI, carboxylated branched PEI, polyDADMAC, other cationic polymers described herein, or a combination thereof). Without wishing to be bound to any particular theory, the miscible blend of photocatalytic multijunction composite ensconced in the cationic polymers leaves a residual self-sanitizing film that kills gram positive bacteria, gram negative bacteria, as well as enveloped and non-enveloped viruses within 30 minutes of contact, and in about 8 hours photocatalytically kills 95% of a *C. difficile* population. This is described in U.S. Provisional Patent Application 62/368,008, filed Jul. 28, 2016 and U.S. Provisional Patent Application 62/488,421, filed April 2017. The disclosures of these provisional patent applications are fully incorporated herein by reference. In some instances, carboxylated branched PEI is added to the photoreactive composition as a surface-coupling material. Without wishing to be bound by any particular theory, such composition will couple the photocatalytic multijunction composite to the substrate but will not provide a cationic kill mechanism, only a photocatalytic kill mechanism.

In some embodiments, the photocatalytic multijunction composite is dispersed in disinfecting wipes. Disinfecting wipes typically contain other harsh chemicals, such as acids and/or hydrogen peroxide, and are designed as a disinfectant that kills on contact, but leaves no residual self-sanitizing film. The addition of the photocatalytic multijunction composite, along with a surface-coupling material (e.g., a carboxylated branched PEI), provides a way for the impregnated wipes to leave a residual-self sanitizing film.

If desired, one or more additional chemical germicidal agents can be added to any of the foregoing embodiments of the photoreactive composition. This option provides an additional chemical killing mechanism to further enhance the antimicrobial activity of the photoreactive composition. When one or more germicidal agents is incorporated into the photoreactive composition, the agent is dispersed as a disinfectant to help "kill now" and may, without wishing to be bound by any particular theory, also be entrapped in the antimicrobial film that can be formed on the surface of a substrate that is incrementally released when the coated surface comes into contact with moisture. Exposing the film to larger amounts of water, such as when the surface is moistened by wiping, food residues, or dishwater, can lead to the release of increased amounts of the germicidal agent. Thus, it is important that the germicidal agents used are non-toxic to humans and should not make the film tacky, hazy or in any way detract from the appearance of the surfaces to which they are applied. The germicidal agents typically are added in lower concentrations. Accordingly, such additives preferably comprise between 0.001% and 5% weight based on monomers ("wbm") of the cationic polymer.

Suitable germicidal agents can be, for example, a strong oxidant (e.g., alkaline metal salts and/or alkaline earth, metal salts of hypochlorous acid, hypochlorous acid, solubilized chlorine, and any source of free chlorine, acidic sodium chlorite, or active chlorine generating compound), chlorhexidine, chlorhexidine gluconate, glutaral, halazone, hexachlorophene, nitrofurazone, nitromersol, povidone-iodine, thimerosol, $C_1$-$C_5$-parabens, hypochlorite salts, clofucarban, clorophen, poloxamer iodine, phenolics, mafenide acetate, aminacrine hydrochloride, quaternary ammonium salts, oxychlorosene, metabromsalan, merbromin, dibromsalan, glyceryl laurate, sodium and/or zinc pyrithione, (dodecyl)(diethylenediamine)glycine, (dodecyl)(aminopropyl)glycine, a phenolic compound, (e.g., m-cresol, o-cresol, p-cresol, o-phenyl-phenol, 4-chloro-m-cresol, chloroxylenol, 6-n-amyl-m-cresol, resorcinol, resorcinol monoacetate, p-tert-butylphenol and o-benzyl-p-chlorophenol), alkaline glutaraldehyde, and a quaternary ammonium salt (e.g., N-(higher) $C_{10}$-$C_{24}$-alkyl-N-benzyl-quaternary ammonium salts that comprise water-solubilizing anions such as halide (e.g., chloride, bromide and iodide), sulfate, and methosulfate, and the heterocyclicimides, such as the imidazolinium salts). Suitable quaternary ammonium compounds are described in U.S. Pat. No. 8,067,403, which is incorporated herein by reference, and include benzalkonium chlorides (e.g., benzalkonium chloride), substituted benzalkonium chlorides (e.g., alkyl dimethyl benzyl ammonium chloride), dual quaternary ammonium compounds (e.g., contain an equal mixture of alkyldimethyl benzyl ammonium chloride and alkyl dimethyl ethylbenzyl ammonium chloride), twin or dual chain quaternary ammonium compounds, such as dialkylmethyl amines (e.g., didecyl dimethyl ammonium chloride or dioctyldimethyl ammonium chloride), and mixtures of fourth generation quaternary ammonium compounds with second-generation quaternary ammonium compounds (e.g., didecyl dimethyl ammonium chloride with alkyl dimethyl benzyl ammonium chloride). In an embodiment, the germicide is at least one member selected from the group consisting of sodium hypochlorite, chloride, chlorine dioxide, sodium chloride, potassium persulfate, potassium permanganate, silver nitrate, chlorhexidine, hexachlorophene, hydrogen peroxide, acetic acid, peracetic acid, betadine, povidone iodine, formaldehyde, glutaraldehyde, benzalkonium chloride, triclosan, boric acid, phenol, cresylic acid, thymol, polyhexamethylbiguanide, and combinations thereof.

In certain embodiments, the photoreactive composition comprises, consists essentially of, or consists of acidified graphitic carbon nitride platelets, a $g-C_3N_4/g-C_3N_4$ heterojunction, a conjugated polymer, a noble metal, a fluorescent dye, carboxylated branched polyethylenimine, and a carrier. In certain embodiments, the photoreactive composition comprises, consists essentially of, or consists of nano rods of acidified graphitic carbon nitride, mesoporous submicron and nanoparticles of a $g-C_3N_4/g-C_3N_4$ heterojunction, a crystalline conjugated polymer, nanoparticles of a noble metal, a fluorescent dye, carboxylated branched polyethylenimine, and a carrier. In some aspects of these embodiments, the conjugated polymer is crystalline poly(3-hexylthiophene) ("P3HT"), the noble metal is platinum, the fluorescent dye is fluorescein, and/or the carrier comprises ethanol and water.

The invention also provides a method of disinfecting a surface comprising applying to the surface a photoreactive composition comprising (a) a photocatalytic multijunction composite comprising at least one photocatalytic heterojunction that is primarily carbon based, (b) at least one surface-coupling material, (c) optionally at least one additive selected from a charge-transfer augmenting material, a light-capturing augmenting material, an antimicrobial augmenting material(s), or a combination thereof, and (d) a carrier, wherein the photocatalytic multijunction is photoreactive in ordinary room lighting. Each of these components is as described herein. The photoreactive composition can further comprise one or more additives, as described herein. As used herein, the term "applying" refers to any suitable technique used to transfer the photoreactive composition to a surface. For example, techniques for applying can be, but are not limited to, brushing, rolling, spraying, wiping, mopping, pouring, painting, absorbing, adsorbing, imbibing, soaking, saturating, permeating, immersing, and a combination of these methods.

Once the photoreactive composition is applied to the surface, the carrier evaporates to leave an antimicrobial film on the surface. The antimicrobial film renders the surface bactericidal, virucidal, germicidal, and/or fungicidal. As used herein, the term "renders the surface bactericidal, virucidal, germicidal, and/or fungicidal" refers to reducing (e.g., eliminating, killing, or preventing and/or inhibiting growth) the presence of bacteria, viruses, germs, and/or fungus (e.g., *Aspergillus brasiliensis* or yeast) to any suitable degree. As used herein, the term "any suitable degree" refers to 50% reduction or more, including 60% reduction or more, 70% reduction or more, 80% reduction or more, 90% reduction or more, 92% reduction or more, 94% reduction or more, 95% reduction or more, 97% reduction or more, 98% reduction or more, 99% reduction or more, or 99.5% elimination or more.

In accordance with this embodiment, the invention provides a coated surface comprising a surface (e.g., a surface of a substrate) and an antimicrobial film, as described herein, that is applied to the surface.

The surface that is rendered bactericidal, virucidal, germicidal, and/or fungicidal can be of any suitable material, including a biocompatible material. The surface can be used in or derived from any suitable form, such as, for example, a powder, dust, an aggregate, an amorphous solid, a sheet, a fiber, a tube, a fabric, or the like. In embodiments, the surface comprises metal, glass, fiberglass, silica, sand, wood, fiber, natural polymer, synthetic polymer, plastic, rubber, ceramic, porcelain, stone, marble, cement, a human or animal body (e.g., skin), or any hybrid, alloy, copolymer, blend, or combination thereof.

Metal surfaces suitable for use in the invention include, for example, stainless steel, nickel, titanium, tantalum, aluminum, copper, gold, silver, platinum, zinc, nickel titanium alloy (nitinol), an alloy of nickel, chromium, and iron (INCONEL™, Special Metals, Corporation, Elkhart, Ind.), iridium, tungsten, silicon, magnesium, tin, galvanized steel, hot dipped galvanized steel, electrogalvanized steel, annealed hot dipped galvanized steel, alloys of any of the foregoing metals, glass, plastics (e.g., polycarbonate, acrylic, and textile), coatings containing any of the foregoing metals, and combinations thereof.

Glass surfaces suitable for use in the invention include, for example, soda lime glass, strontium glass, borosilicate glass, barium glass, glass-ceramics containing lanthanum, fiber glass, and combinations thereof.

Silica surfaces suitable for use in the invention include, for example, quartz, fused quartz, crystalline silica, fumed silica, silica gel, silica aerogel, and mixtures thereof.

Sand surfaces suitable for use in the invention include, for example, sand comprised of silica (e.g., quartz), calcium carbonate (e.g., aragonite), and mixtures thereof. The sand can comprise other components, such as minerals (e.g., magnetite, chlorite, glauconite, gypsum, olivine, garnet), metal (e.g., iron), shells, coral, limestone, and/or rock.

Suitable wood surfaces include, for example, hard wood and soft wood, and materials engineered from wood, wood chips, or fiber (e.g., plywood, oriented strand board, laminated veneer lumber, composites, strand lumber, chipboard, hardboard, medium density fiberboard), and combinations thereof. Types of wood include alder, birch, elm, maple, willow, walnut, cherry, oak, hickory, poplar, pine, fir, and combinations thereof.

Fiber surfaces suitable for use in the invention include, for example, natural fibers (e.g., derived from an animal, vegetable, or mineral) and synthetic fibers (e.g., derived from cellulose, mineral, or polymer). Suitable natural fibers include cotton, hemp, jute, flax, ramie, sisal, bagasse, wood fiber, silkworm silk, spider silk, sinew, catgut, wool, sea silk, wool, mohair, angora, and asbestos. Suitable synthetic fibers include rayon (e.g., lyocell), modal, and metal fiber (e.g., copper, gold, silver, nickel, aluminum, iron), carbon fiber, silicon carbide fiber, bamboo fiber, seacell, nylon, polyester, polyvinyl chloride fiber (e.g., vinyon), polyolefin fiber (e.g., polyethylene, polypropylene), acrylic polyester fiber, aramid (e.g., TWARON™, KEVLAR™, or NOMEX™), spandex, and combinations thereof.

Natural polymer surfaces suitable for use in the invention include, for example, a polysaccharide (e.g., cotton, cellulose), shellac, amber, wool, silk, natural rubber, a biopolymer (e.g., a protein, an extracellular matrix component, collagen), and combinations thereof.

Synthetic polymer surfaces suitable for use in the invention include, for example, polyvinylpyrrolidone, acrylics, acrylonitrile-butadiene-styrene, polyacrylonitrile, acetals, polyphenylene oxides, polyimides, polystyrene, polypropylene, polyethylene, polytetrafluoroethylene, polyvinylidene fluoride, polyvinyl chloride, polyethylenimine, polyesters, polyethers, polyamide, polyorthoester, polyanhydride, polysulfone, polyether sulfone, polycaprolactone, polyhydroxybutyrate valerate, polylactones, polyurethanes, polycarbonates, polyethylene terephthalate, as well as copolymers and combinations thereof.

Typical rubber surfaces suitable for use in the invention include, for example, silicones, fluorosilicones, nitrile rubbers, silicone rubbers, polyisoprenes, sulfur-cured rubbers, butadiene-acrylonitrile rubbers, isoprene-acrylonitrile rubbers, and combinations thereof.

Ceramic surfaces suitable for use in the invention include, for example, boron nitrides, silicon nitrides, aluminas, silicas, and combinations thereof.

Stone surfaces suitable for use in the invention include, for example, bauxite, calcite, feldspar, gypsum, slate, granite, quartz, quartzite, limestone, dolostone, sandstone, marble, soapstone, serpentine and combinations thereof.

For purposes of the present invention, animal bodies include, but are not limited to, the order Rodentia (e.g., mice), the order Logomorpha (e.g., rabbits), the order Carnivora (e.g., Felines (cats) and Canines (dogs)), the order Artiodactyla (e.g., Bovines (cows) and Swines (pigs)), the order Perssodactyla (e.g., Equines (horses)), the order Primates, Ceboids, or Simioids (e.g., monkeys), the class Ayes (e.g., birds), the class of Phylum Arthropoda (e.g., insects), or the order Anthropoids (e.g., humans and apes). Typically skin (including intact skin, wounded or broken skin, and/or skin that is otherwise damaged, by for example, a burn) and/or mucosal tissue (e.g., oral, nasal, ocular, or genital tissue) of the animal body serves as the surface suitable for application of the photoreactive composition. The skin and/or mucosal tissue can be associated with any part of the animal body, including the limbs, tail, abdomen, chest, head, neck, face, genital area (e.g., udder), buttocks, or back. In general, the type and amount of components of the photoreactive composition will be selected to ensure biocompatibility, to minimize toxicity, to minimize irritation, and/or have a desired level of surface tack and/or adhesiveness of the formed film.

The surface typically is a component of a larger structure. For example, the surface can be part of a substrate, such as a medical device, diagnostic equipment, implant, glove, mask, curtain, mattress, sheets, blankets, gauze, dressing, tissue, surgical drape, tubing, surgical instrument, safety gear, fabric, apparel item, floor, handles, wall, sink, shower or tub, toilet, furniture, wall switch, toy, athletic equipment, playground equipment, shopping cart, countertop, appliance, railing, door, air filter, pipe, utensil, dish, cup, container, object display container, food, food display container, food package, food processing equipment, food handling equipment, food transportation equipment, food vending equipment, food storage equipment, food packaging equipment, plant, phone, cell phone, remote control, computer, mouse, keyboard, touch screen, leather, cosmetic, cosmetic making equipment, cosmetics storage equipment, cosmetics packaging equipment, personal care item, personal care item making equipment, personal care storage equipment, personal care packaging equipment, animal care item, animal care item making equipment, veterinary equipment, powder, cream, gel, salve, eye care item, eye care item making equipment, contact lens, glasses, eye care storage equipment, contact lens case, jewelry, jewelry making equipment, jewelry storage equipment, animal housing, farming equipment, animal food handling equipment, animal food storage space, animal food storage equipment, animal food container, air vehicle, land vehicle, air processing equipment, air filter, water vehicle, water storage space, water storage equipment, water processing equipment, water storage container, water filter, hand, hair, foot, leg, arm, torso, head, or animal body part, pharmaceuticals display container, pharmaceuticals package, pharmaceuticals processing equipment, pharmaceuticals handling equipment, pharmaceuticals transportation equipment, pharmaceuticals vending equipment, pharmaceuticals, pharmaceuticals storage equipment, pharmaceuticals packaging equipment.

A "medical device" includes any device having surfaces that contact tissue, blood, or other bodily fluids in the course of their use or operation, which are found on or are subsequently used within a mammal (e.g., a human). Medical devices include, for example, extracorporeal devices for use in surgery, such as blood oxygenators, blood pumps, blood storage bags, blood collection tubes, blood filters including filtration media, dialysis membranes, tubing used to carry blood and the like which contact blood which is then returned to the patient or mammal. Medical devices also include endoprostheses implanted in a mammal (e.g., a human), such as vascular grafts, stents, pacemaker leads, surgical prosthetic conduits, heart valves, and the like, that are implanted in blood vessels or the heart. Medical devices also include devices for temporary intravascular use such as catheters, guide wires, amniocentesis and biopsy needles, cannulae, drainage tubes, shunts, sensors, transducers, probes and the like which are placed into the blood vessels, the heart, organs or tissues for purposes of monitoring or repair or treatment. Medical devices also include prostheses such as artificial joints such as hips or knees as well as artificial hearts. In addition, medical devices include penile implants, condoms, tampons, sanitary napkins, ocular lenses, sling materials, sutures, hemostats used in surgery, antimicrobial materials, surgical mesh, transdermal patches, and wound dressings/bandages.

The "diagnostic equipment" includes any device or tool used to diagnose or monitor a medical condition. Examples include an ultrasound, magnetic resonance imaging (MRI) machine, positron emission tomography (PET) scanner, computed tomography (CT) scanner, ventilator, heart-lung machine, extracorporeal membrane oxygenation (ECMO) machine, dialysis machine, blood pressure monitor, otoscope, ophthalmoscope, stethoscope, sphygmomanometer, blood pressure cuff, electrocardiograph, thermometer, defibrillator, speculum, sigmoidoscope, and anoscope.

The "surgical instrument" includes any tool or device used for performing surgery or an operation. Examples include a scalpel, lancet, trocar, hemostat, grasper, forceps, clamp, retractor, distractor, positioner, tracheotome, dilator, stapler, irrigation needle, injection needle, drill, scope, endoscope, probe, ruler, and caliper.

"Safety gear" includes devices used to protect a person, animal, or object. Examples of "safety gear" are a mask, face shield, visor, goggles, glasses, gloves, shoe covers, foot guard, leg guard, belt, smock, apron, coat, vest, raingear, hat, helmet, chin strap, hairnet, shower cap, hearing protection (ear plugs, ear muffins, hearing bands), respirator, gas mask, supplied air hood, collar, leash, and first aid kit.

"Fabric" includes any type of suitable fabric, such as bedding, curtains, towels, table coverings, protective sheeting, and dish cloths.

An "apparel item" includes an item of clothing, footwear, or other item someone would wear on his/her person. Examples include a uniform, coat, shirt, pants, waders, scrubs, socks, shoe or boot liner, an insole, gloves, hats, shoes, boots, and sandals.

The surface can be part of a building structure or an item that can be found in a building structure, such as a floor, wall, an appliance (e.g., a refrigerator, oven, stove, dishwasher, washing machine, clothes dryer, furnace, water heater, air conditioner, heater), sink, shower or tub, toilet, furniture (e.g., mattress, couch, sofa, chair, table, shelf, mantle, bed, dresser), countertop, railing, air filter, air processing equipment, water processing equipment, water filter, pipe, door, handle, light, light switch, thermostat, sprinkler, air conditioner evaporator and/or condenser.

The surface can also be a toy or athletic equipment, including exercise equipment, playground equipment, or a pool.

The surface can be a utensil (e.g., knife, fork, spoon, ladle, spatula, whisk, etc.), a dish (e.g., a food storage container, a food serving piece, etc.), a food package (e.g., a bag, a box, foil, plastic wrap), or other item that comes in contact with food (e.g., a cutting board, food display container, food processing equipment, food handling equipment, food transportation equipment, food vending equipment, animal food handling equipment, animal food storage space, food storage equipment, animal food container, animal food storage equipment). The surface can be part of food processing equipment, such as food processing tanks, stirrers, conveyor belts, knives, grinders, packaging machines, labeling machines, etc.

The "food" is any food in which it would be desirable to provide with an antimicrobial film. In such embodiments, the antimicrobial film and the composition thereof should be nontoxic for human and animal consumption. The "food" can be, e.g., any fruit, vegetable, meat, or egg.

The "plant" is any suitable plant, including an angiosperm (a flowering plant), gymnosperm (a seed-producing plant), a conifer, fern, and moss. Suitable angiosperms are from the *amborella* (e.g., *Amborella trichopoda Baill*), nymphaeales (e.g., water lily), austrobaileyales (e.g., *Illicium verum*), chloranthales (e.g., from the genus ascarina, chloranthus, hedyosmum, or sarcandra), magnoliids (e.g., *magnolia*, bay laurel, black pepper), monocots (e.g., grasses, orchids, palms), ceratophyllum (e.g., aquatic plants), or eudicots (e.g., sunflower, *petunia*, apple) groups. Suitable gymnosperms are from the subclass cycadidae, ginkgoidae, gnetidae, or pinidae.

The surface can be part of an electronic device, such as a phone, cell phone, remote control, computer, mouse, keyboard, or touch screen.

The surface can further be part of a cosmetic (e.g., eye shadow, eyeliner, primer, foundation, lipstick, lip gloss, blush), cosmetic making equipment, cosmetic storage equipment, cosmetic packaging equipment, a personal care item (e.g., cream, gel, salve, lip balm, body soap, facial soap, lotion, cologne, perfume, antiperspirant, deodorant, facial tissue, cotton swabs, cotton pads, mouthwash, toothpaste, nail polish, shampoo, conditioner, hairspray, talcum powder, shaving cream, contact lens, contact lens case, glasses), personal care item making equipment, personal care storage equipment, personal care packaging equipment, jewelry (e.g., necklace, ring, earring, bracelet, watch), jewelry making equipment, or jewelry storage equipment.

The "animal care item" and "veterinary equipment" can be any product used in a setting that includes animals, such as a house, boarding house, or veterinary hospital. Of course, veterinary equipment can be used at a location outside of a hospital setting. Animals are any animals that are typically considered pets, non-pets, boarded, treated by a veterinarian, and animals in the wild. Examples include a dog, cat, reptile, bird, rabbit, ferret, guinea pig, hamster, rat, mouse, fish, turtle, horse, goat, cattle, and pigs. Suitable animal care items include the personal care items described herein, toys, bed, crate, kennel, carrier, bowl, dish, leash, collar, litterbox, and grooming items (e.g., clippers, scissors, a brush, comb, dematting tool, and deshedding tool). Suitable veterinary equipment includes any of the medical devices and surgical instruments described herein and other equipment, such as a table, tub, stretcher, sink, scale, cage, carrier, and leash.

The "animal housing" can be any suitable housing, such as a coop, stable, shelter, grab bag shelter, hutch, barn, shed, pen, nestbox, feeder, stanchion, cage, carrier, or bed.

The "farming equipment" is any device used in an agricultural setting, including a farm or ranch, particularly a farm or ranch that houses animals, processes animals, or both. Animal livestock that can be housed or processed as described herein and include, e.g., horses, cattle, bison, and small animals such as poultry (e.g., chickens, quails, turkeys, geese, ducks, pigeons, doves, pheasants, swan, ostrich, guineafowl, Indian peafowl, emu), pigs, sheep, goats, alpacas, llamas, deer, donkeys, rabbits, and fish. Examples of farming equipment include as a wagon, trailer, cart, barn, shed, fencing, sprinkler, shovel, scraper, halter, rope, restraining equipment, feeder, waterer, trough, water filter, water processing equipment, stock tank, fountain, bucket, pail, hay rack, scale, poultry flooring, egg handling equipment, a barn curtain, tractor, seeder, planter, plow, rotator, tiller, spreader, sprayer, agitator, sorter, baler, harvester, cotton picker, thresher, mower, backhoe loader, squeeze chute, hydraulic chute, head chute, head gate, crowding tub, corral tub, alley, calving pen, calf table, and milking machine.

The surface can be part of a vehicle, such as an air vehicle, land vehicle, or water vehicle. Suitable vehicles include a car, van, truck, bus, ambulance, recreational vehicle, camper, motorcycle, scooter, bicycle, wheelchair, train, streetcar, ship, boat, canoe, submarine, an unmanned underwater vehicle (UUV), a personal water craft, airplane, jet, helicopter, unmanned autonomous vehicle (UAV), and hot air balloon.

If desired, the surface to which the antimicrobial film has been applied can be regenerated by removing the antimicrobial film. The removing can be performed by any suitable step, such as washing or rinsing with a solvent (e.g., water and/or alcohol). Thus, the antimicrobial coating on a surface (e.g., the surface of a substrate) described herein can be considered temporary (e.g., removable).

The antimicrobial film renders the surface bactericidal against any suitable bacteria to any suitable degree. In other words, a photoreactive composition of the present invention can form an antimicrobial film on a surface (e.g., the surface of a substrate) that kills at least 75% (e.g., at least 80%, at least 85%, at least 90%, at least 92%, at least 94%, at least 95%, at least 96%, at least 97%, at least 98%, at least 99%, or at least 99.5%) of bacteria that comes in contact with the antimicrobial film. For example, the bacteria can be, for example, *Staphylococcus aureus*, gram positive methicillin-resistant *Staphylococcus aureus* (MRSA), *Staphylococcus saprophyticus, Pseudomonas aeruginosa, Listeria monocytogenes, Klebsiella pneumoniae, Streptococcus pneumoniae, Streptococcus pyogenes, Streptococcus agalactiae, Haemophilus influenzae, Helicobacter pylori, Salmonella,*

*Shigella, Clostridium, Enterobacter aerogenes*, gram negative *Escherichia coli, Clostridium difficile*, or a combination thereof. In certain embodiments, the photoreactive composition is effective in reducing (e.g., eliminating, killing, or preventing and/or inhibiting growth) gram positive methicillin-resistant *Staphylococcus aureus* (MRSA), gram negative *Escherichia coli* (ATCC 8739), *Clostridium difficile* (ATCC 43598), or a combination thereof.

In an aspect of the invention, an antimicrobial film formed from a photoreactive composition described herein renders the surface bactericidal against gram positive methicillin-resistant *Staphylococcus aureus* (MRSA) bacteria. Preferably, the antimicrobial film kills at least 95% (e.g., at least 96%, at least 97%, at least 98%, at least 99%) of a log 5 population of gram positive methicillin-resistant *Staphylococcus aureus* (MRSA) bacteria within 30 minutes (e.g., within 20 minutes, within 15 minutes, within 10 minutes, within 5 minutes) of contact. In a particularly preferred embodiment, the antimicrobial film kills at least 99.8% of a log 5 population of gram positive methicillin-resistant *Staphylococcus aureus* (MRSA) bacteria within 5 minutes of contact.

In another aspect of the invention, an antimicrobial film formed from a photoreactive composition described herein renders the surface bactericidal against gram negative *Escherichia coli* (ATCC 8739) bacteria. In particular, the antimicrobial film kills at least 95% (e.g., at least 96%, at least 97%, at least 98%, at least 99%) of a log 5 population of gram negative *Escherichia coli* (ATCC 8739) bacteria within 30 minutes (e.g., within 20 minutes, within 15 minutes, within 10 minutes, within 5 minutes) of contact. In a preferred embodiment, the antimicrobial film kills at least 95% of a log 5 population of gram negative *Escherichia coli* (ATCC 8739) bacteria within 5 minutes of contact.

In yet another aspect of the invention, an antimicrobial film formed from a photoreactive composition described herein renders the surface bactericidal against *Clostridium difficile* (ATCC 43598) bacteria. More specifically, the antimicrobial film kills at least 75% (e.g., at least 80%, at least 85%, at least 90%, at least 95%, at least 97%, at least 98%, at least 99%) of a log 4 population of *Clostridium difficile* (ATCC 43598) bacteria within 24 hours (e.g., within 18 hours, within 12 hours, within 10 hours, within 8 hours, within 6 hours) of contact. In a preferred embodiment, the antimicrobial film kills at least 99.7% of a log 4 population of *Clostridium difficile* (ATCC 43598) bacteria within 8 hours of contact.

Viruses are much more difficult to kill, especially non-enveloped viruses, e.g., norovirus, rotavirus, adenovirus, and poliovirus. Generally, the only way to kill an array of non-enveloped viruses is with an abundance of very harsh chemicals, such as hypochlorite, acids, and peroxides, all of which are highly cytotoxic. Remarkably, the technology described in the present invention, when imbued in the cationic material described herein or in the concurrently filed patent application by the same applicant and entitled "Polymer-based Antimicrobial Compositions and Methods of Use Thereof," which is hereby incorporated by reference in its entirety, is capable of forming antimicrobial films that kill non-enveloped viruses. Accordingly the present invention provides an antimicrobial film formed from a photoreactive composition described herein that renders a surface virucidal against any suitable virus to any suitable degree, such as, reducing (e.g., eliminating, killing, or preventing and/or inhibiting growth) at least 75% (e.g., at least 80%, at least 85%, at least 90%, at least 92%, at least 94%, at least 95%, at least 96%, at least 97%, at least 98%, at least 99%, or at least 99.5%) of the virus. In a particular example, an antimicrobial film formed from a photoreactive composition described herein renders the surface virucidal against at least one enveloped virus (e.g., chickenpox virus, influenza, herpes simplex, severe acute respiratory syndrome (SARS), flavivirus, togavirus) and/or non-enveloped virus (e.g., levivirus, norovirus, rotavirus, adenovirus, parvovirus, and poliovirus).

In another aspect of the invention, an antimicrobial film formed from a photoreactive composition described herein renders the surface virucidal against influenza A (e.g., H1N1, H1N2, and H5N1) enveloped virus. In an embodiment, the antimicrobial film kills at least 95% (e.g., at least 96%, at least 97%, at least 98%, at least 99%) of a log 4 population of influenza A (H1N1) (ATCC CCL-34) enveloped virus within 60 minutes (e.g., within 45 minutes, within 30 minutes, within 20 minutes) of contact. In a preferred embodiment, the antimicrobial film kills at least 99% of a log 4 population of influenza A (H1N1) (ATCC CCL-34) enveloped virus within 30 minutes of contact.

In yet another aspect of the invention, an antimicrobial film renders the surface virucidal against a non-enveloped virus (e.g., MS2, which is used as a surrogate), norovirus, rotavirus, adenovirus, parvovirus, or poliovirus. In an embodiment, the antimicrobial film kills at least 95% (e.g., at least 96%, at least 97%, at least 98%, at least 99%) of a non-enveloped virus within 30 minutes (e.g., within 20 minutes, within 15 minutes, within 10 minutes, within 5 minutes) of contact. In a preferred embodiment, the antimicrobial film kills at least 97% of a non-enveloped virus within 5 minutes of contact. In some instances of this embodiment, the non-enveloped virus is MS2 (ATCC 15597-B1).

The antimicrobial film renders the surface fungicidal against any suitable fungus to any suitable degree. In other words, a photoreactive composition of the present invention can form an antimicrobial film on a surface (e.g., the surface of a substrate) that kills at least 75% (e.g., at least 80%, at least 85%, at least 90%, at least 92%, at least 94%, at least 95%, at least 96%, at least 97%, at least 98%, at least 99%, or at least 99.5%) of fungus that comes in contact with the antimicrobial film. For example, the fungus can be a species of *Aspergillus, Blastomyces, Candida, Coccidioides, Cryptococcus, Histoplasma, Mucormycetes, Pneumoncystis, Sporothrix, Exserohilum, Cladosporium*, or a combination thereof. In certain embodiments, the photoreactive composition is effective in reducing (e.g., eliminating, killing, or preventing and/or inhibiting growth) at least 80% of a log 4 population of *Aspergillus brasiliensis* fungus within 12 hours of contact. In certain embodiments, the photoreactive composition is effective in reducing at least 90% of a log 4 population of yeast within 24 hours of contact.

The invention is further illustrated by the following embodiments.

(1) A photoreactive composition comprising: (a) a photocatalytic multijunction composite comprising at least one photocatalytic heterojunction that is primarily carbon based, (b) at least one surface-coupling material, (c) optionally at least one additive selected from a charge-transfer augmenting material, a light-capturing augmenting material, an antimicrobial augmenting material(s), or a combination thereof, and (d) a carrier, wherein the photocatalytic multijunction is photoreactive in ordinary room lighting.

(2) The photoreactive composition of embodiment (1), wherein the photocatalytic heterojunction that is primarily carbon based comprises an organic material selected from graphitic carbon nitride, acidified carbon nitride (ACN), graphene oxide, reduced graphene oxide, a conjugated polymer, and a combination thereof.

(3) The photoreactive composition of embodiment (1) or (2), wherein the photocatalytic multijunction composite comprises inorganic material(s) that are selected from a transition metal oxide, a transition metal sulfide, a transition metal selenide, an alloy comprising copper, indium, gallium, and diselenide (CIGS), and combinations thereof.

(4) The photoreactive composition of embodiment (3), wherein the inorganic material(s) are selected from cadmium sulfide (CdS), cadmium selenide (CdSe), an alloy comprising copper, indium, gallium, and diselenide (CIGS), and combinations thereof.

(5) The photoreactive composition of any one of embodiments (1)-(4), wherein the photocatalytic multijunction composite has (i) one or more conduction band(s) more negative than about −0.42 eV at pH 7, (ii) one or more valence band(s) more positive than about +0.81 eV at pH 7, or (iii) both (i) and (ii).

(6) The photoreactive composition of any one of embodiments (1)-(5), wherein the photocatalytic multijunction composite comprises one or more organic material(s) and one or more inorganic material(s), such that the charge transfer from the valence band is uphill, and the charge transfer from the conduction band is downhill.

(7) The photoreactive composition of any one of embodiments (1)-(6), wherein the photocatalytic multijunction composite photocatalytically oxidizes water to form hydroxy radicals.

(8) The photoreactive composition of any one of embodiments (1)-(7), wherein the photocatalytic multijunction composite photocatalytically reduces water to form superoxide anions.

(9) The photoreactive composition of any one of embodiments (1)-(8), wherein the photocatalytic multijunction composite comprises one or more crystalline components.

(10) The photoreactive composition of any one of embodiments (1)-(9), wherein the photocatalytic multijunction composite comprises one or more platelet component(s), one or more nano rod component(s), or a combination thereof.

(11) The photoreactive composition of any one of embodiments (1)-(10), wherein the photocatalytic multijunction composite comprises one or more mesoporous component(s).

(12) The photoreactive composition of any one of embodiments (9)-(11), wherein the crystalline component, platelet component, nano rod component, and/or mesoporous component are sub-micron particles.

(13) The photoreactive composition of any one of embodiments (1)-(12), wherein the at least one surface-coupling material has an attractive force to a surface, the photocatalytic multijunction composite, or both.

(14) The photoreactive composition of embodiment (13), wherein the at least one surface-coupling material is a low-work function material.

(15) The photoreactive composition of embodiment (13) or (14), wherein the at least one surface-coupling material is a titanate, a silane, a carboxylated branched polyethylenimine-based polymer, a carboxylated linear polyethylenimine-based polymer, a polyethylenimine-based polymer, cationic block copolymers, other polymers modified with one or more acyl groups and/or carboxylic acid groups, salts of any of the foregoing, or a combination thereof.

(16) The photoreactive composition of embodiment (15), wherein the surface-coupling material is a carboxylated branched polyethylenimine-based polymer.

(17) The photoreactive composition of any one of embodiments (1)-(16), wherein the additive is present and is a charge-transfer augmenting material.

(18) The photoreactive composition of embodiment (17), wherein the charge-transfer augmenting material is a noble metal selected from ruthenium, rhodium, palladium, silver, osmium, iridium, platinum, gold, or a combination thereof.

(19) The photoreactive composition of embodiment (17) or (18), wherein the charge-transfer augmenting material is a conjugated polymer selected from poly(3-hexylthiophene) (P3HT), polypyrrole (Ppy), polycarbazole, polyindole, polyazepine, polyaniline, polyfluorene, polyphenylene, polypyrene, polyazulene, polynaphthalene, polythiophene (Ptp), poly(3,4-ethylenedioxythiophene), poly(p-phenylene sulfide), polyacetylene, poly(p-phenylene vinylene), and a combination thereof.

(20) The photoreactive composition of any one of embodiments (1)-(19), wherein the additive is present and is a light-capturing augmenting material that is a dye molecule selected from fluorescein, fluorescein isothiocyanate, a cyanine, a merocyanine, a hemicyanine, a perylene, a xanthene, a porphyrin, a phthalocyanine, a polyene, a polythiophene, a coumarin, a ruthenium-based dye, and a combination thereof.

(21) The photoreactive composition of any one of embodiments (1)-(20), wherein the additive is present and is an antimicrobial augmenting material.

(22) The photoreactive composition of embodiment (21), wherein the antimicrobial augmenting material is a cationic polymer.

(23) The photoreactive composition of embodiment (22), wherein the cationic polymer is a linear polyethylenimine-based polymer, polydiallyldimethylammonium chloride (polyDADMAC), or poly(acrylamide-co-diallyldimethylammonium chloride).

(24) The photoreactive composition of any one of embodiments (17)-(23), wherein the additive is dispersed on the outer edge of the photocatalytic multijunction composite, on the surface of the photocatalytic multijunction composite, in the carrier, or a combination thereof.

(25) The photoreactive composition of embodiment (1), wherein the photoreactive composition comprises acidified graphitic carbon nitride platelets (ACN), a $g\text{-}C_3N_4/g\text{-}C_3N_4$ heterojunction, a conjugated polymer, a noble metal, a fluorescent dye, carboxylated branched polyethylenimine, and a carrier.

(26) The photoreactive composition of embodiment (25), wherein the photoreactive composition comprises nano rods of acidified graphitic carbon nitride, mesoporous submicron and nanoparticles of a $g\text{-}C_3N_4/g\text{-}C_3N_4$ heterojunction, a crystalline conjugated polymer, nanoparticles of a noble metal, a fluorescent dye, carboxylated branched polyethylenimine, and a carrier.

(27) The photoreactive composition of embodiment (26), wherein the conjugated polymer is crystalline poly(3-hexylthiophene) (P3HT), the noble metal is platinum, the fluorescent dye is fluorescein, and the carrier comprises ethanol and water.

(28) A method of disinfecting a surface comprising applying to the surface the photoreactive composition of any one of embodiments (1)-(27).

(29) The method of embodiment (28), wherein the carrier evaporates to leave an antimicrobial film on the surface and renders the surface bactericidal, virucidal, germicidal, and/or fungicidal.

(30) The method of embodiment (29), wherein the antimicrobial film kills at least one of the following: (i) at least 95% of a log 5 population of gram positive methicillin-resistant *Staphylococcus aureus* (MRSA) bacteria within 30 minutes of contact; (ii) at least 95% of a log 5 population of gram negative *Escherichia coli* (ATCC 8739) bacteria within 30 minutes of contact; (iii) at least 95% of a log 4 population of influenza A (H1N1) (ATCC CCL-34) enveloped virus within 60 minutes of contact; (iv) at least 95% of a non-enveloped virus within 30 minutes of contact; (v) at least 90% of a log 4 population of *Clostridium difficile* (ATCC 43598) bacteria within 24 hours of contact; (vi) at least 80% of a log 4 population of *Aspergillas brasliensis* fungus within 12 hours of contact; and/or (vii) at least 90% of a log 4 population of yeast within 24 hours of contact.

The following examples further illustrate the invention but, of course, should not be construed as in any way limiting its scope.

EXAMPLES

Example 1

This example provides an exemplary procedure for the preparation of the photoreactive compositions described herein.

Step 1: Construction of the Mesoporous Heterojunction ($CN_1/CN_2$)

A mesoporous heterojunction $CN_1/CN_2$ was formed using simultaneous thermo-polymerization of urea and of thiourea, which creates two different phases that enable the formation of an isotype heterojunction at the interface of the two different phases. This $CN_1/CN_2$ heterojunction comprises two different band structures, leading to the enhanced photocatalytic activity arising from promoted charge separation. For a typical synthesis, 6 g of thiourea and 6 g of urea were dissolved with 30 mL water in an alumina crucible. The solution of urea and thiourea was then dried at 60° C. overnight to get the molecular composite precursor. The molecular composite precursors in a semi-closed alumina crucible were heated to 550° C. at a heating rate of 15° C. $min^{-1}$ in a kiln and maintained for 2 h. After the reaction, the alumina crucible was cooled down to room temperature. The resultant $g-C_3N_4/g-C_3N_4$ mesoporous heterojunction ($CN_1/CN_2$) was collected for further use.

Step 2: The (CN1/CN2) Heterojunction Component is Made Even More Photocatalytic Through Oxidation The performance of the heterojunction was further improved by chemical oxidation. More particularly, 1 g of the obtained ($CN_1/CN_2$) material was added to a beaker. To which was added a mixture of 50 mL of $H_2O_2$ and 10 mL of $NH_3$:$H_2O$, and then the beaker was covered while a suspension was formed. The beaker was then placed in a heating mantle at 60° C. and the suspension in the beaker was stirred until no obvious liquid was left. The obtained sample was washed with deionized water three times. The activated ($CN_1/CN_2$) was obtained after drying the washed sample at 60° C. for 24 hours.

Step 3: Milling to Reduce Surface Defects

The ($CN_1/CN_2$) was subjected to 4 hours of ball milling in a planetary mill with a 10:1 mixture of ($CN_1/CN_2$) to 5 mm balls, rotating at 350 rpm. This technique removed the amino group-structural defects that are created by incomplete polymerization of $g-C_3N_4$, which is believed to reduce the photocatalytic activity of $g-C_3N_4$.

Step 4: Sonication

A cup of 1.75 g of milled ($CN_1/CN_2$) was dispersed in 90 mL of methanol and sonicated with high energy sonication for 5 min. This further reduces the particles to sub-micron and nano particles.

Step 5: Acidification of $g-C_3N_4$ to Create $g-C_3N_4$ Platelets (ACN)

A modified method for preparing $g-C_3N_4$ platelets is used, as compared to the techniques reported by Tong et al. (*RSC Adv.*, 2015, 5, 88149-88153).

The $g-C_3N_4$ platelets were created using bulk $g-C_3N_4$ that was prepared by direct pyrolysis of melamine in a semi-closed system. More specifically, 10 g of melamine was placed in a 50 mL crucible. The crucible was wrapped up with aluminum-foil and heated to 550° C. in a tube furnace for 4 h with a heating rate of 5° C./min, and the cooling rate was controlled at around 2° C./min. The resulting light yellow agglomerate (6 g) was milled into powder in an agate mortar.

The platelets were created using (1 g) of the as-prepared $g-C_3N_4$, which was mixed with 15 mL of concentrated $H_2SO_4$ (98 wt %) in a 100 mL flask and stirred for 15 min. Then, 0.5 mL distilled water was added to the suspension dropwise with stirring, and the temperature of the suspension was rapidly increased to 60° C. due to the simultaneous exothermic process. Water (4.5 mL) was then slowly added into the suspension over 10 min to maintain a constant temperature, and the color of the suspension turned from light yellow to a hazy yellow due to its Tyndall effect. The resulting suspension was poured into 500 mL of distilled water, and a white precipitate was obtained. After the precipitate was fully decanted, all but 200 mL of the final collected decantation from water was poured into 300 mL of methanol, then decanted again which gave rise to a higher percentage of platelets. The total volume of 500 mL was evaporated with a rotary vacuum evaporator to remove all water. Then a 95:5 (% v/v) mixture of methanol to water was added for clean out. The mixture was filtered with 0.7 micro filters, and the filtrate contained an abundance of $g-C_3N_4$ platelets, approximately 3 g/50 mL.

Step 6: Coupling the ACN to ($CN_1/CN_2$) Heterojunction

Coupling the ACN to create the ACN/($CN_1/CN_2$) composite was achieved as follows: 1.75 g of ($CN_1\backslash CN_2$) was dispersed in a 95:5 (% v/v) mixture of methanol to water. ACN (created in Step 5) was added to the resulting dispersion to provide 30 wt % of ACN based on the overall mixture. The pH of the mixture was adjusted to an operational pH of 6.2. The ACN and $g-C_3N_4$ suspended solution was stirred vigorously for 6 h. After volatilization of the ethanol, a yellow powder was obtained upon drying at 50° C. overnight.

Step 7: Adding P3HT

The P3HT/ACN/($CN_1/CN_2$) composite was fabricated at room temperature. The yellow powder (1.75 g of ACN/($CN_1/CN_2$)) obtained in Step 6 was mixed with a P3HT solution (1.0 g/L in chloroform; 3 mL). The mixture was stirred for 12 h, the resultant suspension was evaporated using rotary evaporation, and the solid material placed in the oven to dry at 60° C. for 2 hours. The obtained material was hand ground with mortar and pestle to obtain a purple powder ready for the addition of Pt.

Step 8: Adding Pt to the P3HT/ACN/($CN_1/CN_2$) Multijunction

The purple powder obtained in Step 7 (0.5 g of P3HT/ACN/($CN_1/CN_2$)) was dispersed in 80 mL of ethylene glycol and ultrasonicated in a bath for 30 min. A 2 wt % hexachloroplatinic (IV) acid hexahydrate ($H_2PtCl_6.6H_2O$, 99.9%) solution in ethylene glycol, was added dropwise into the P3HT/ACN/($CN_1/CN_2$) suspension under magnetic stirring. The mixed solution was subsequently refluxed into a two necked round bottom flask fitted in a heating mantle under continuous magnetic stirring at 150° C. for 2 h. After cooling to room temperature, the Pt/P3HT/ACN/($CN_1/CN_2$) photocatalyst was harvested by centrifugation at 10,000 rpm for 30 min and washed thoroughly with a 50:50 (% v/v) mixture of methanol to water three times. Finally, the product was dried in an oven at 70° C. overnight.

Step 9: Adding Dye to the Final Multijunction Composite

The catalyst powder from Step 8 was dispersed in a 2 wt % aqueous dispersion of fluorescence dye (e.g., fluorescein), having pH of 5.5. The catalyst was submerged in the dye for 15 minutes, then centrifuged for 30 minutes, and dried in the oven overnight at 60° C.

Step 10: Dispersing the Multijunction Composite into an Antimicrobial Film

The photocatalytic composition of this example was designed specifically to create light activated antimicrobial films by dispersing the photocatalytic multijunction composite and a surface-coupling material (e.g., carboxylated branched PEI) in an alcohol/water dispersion of an appropriate film-forming polymer or polymers. An appropriate film-forming polymer means a polymer that will not block or mask electron transfer from the catalyst to moisture from the air, which is split by the photocatalytic material to create reactive oxygen species, which in turn oxidizes pathogenic microbes, particularly *Clostridium difficile* and other spore forming pathogens.

Example 2

This example demonstrates the ability of a photoreactive composition (Antimicrobial Photoreactive Composition 1) comprising acidified g-$C_3N_4$ (ACN), a g-$C_3N_4$ heterojunction ($CN_1/CN_2$), poly(3-hexylthiophene) (P3HT) conjugated polymer, platinum, and fluorescein, as prepared according to Example 1, to harvest light and maintain photocatalytic activity and inactivate *Clostridium difficile* spores.

Figure 3:
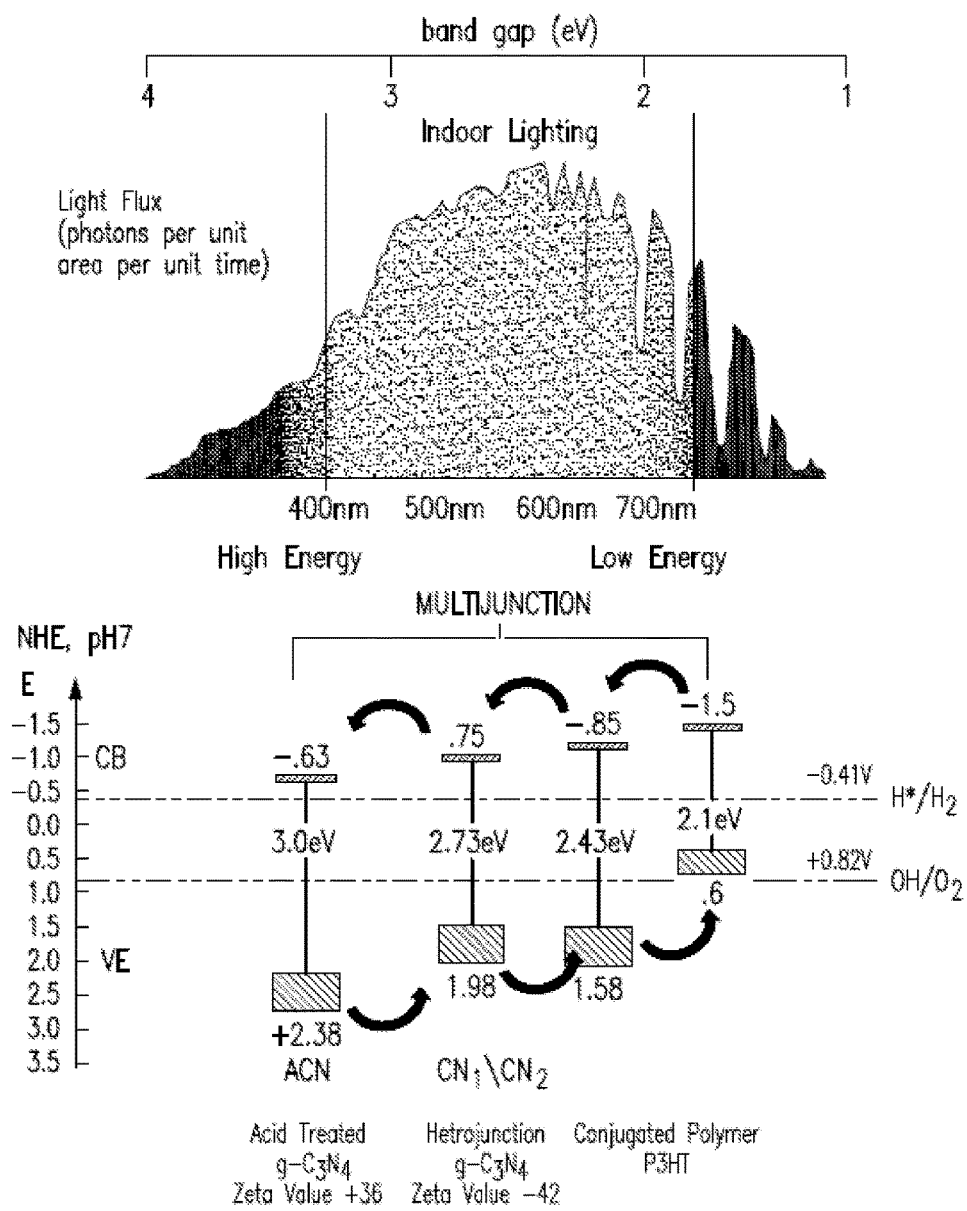
FIG. 3 illustrates the light harvesting ability of a multijunction composite comprising ACN, a $g-C_3N_4$ heterojunction ($CN_1/CN_2$), and poly(3-hexylthiophene) (P3HT).

The photocatalytic composition described in this example is a photocatalytic multijunction composite designed with band gaps to maximize light harvesting in the visible light spectrum. The components of the composite are photocatalytic polymers judiciously synthesized, and assembled, to capture three broad slices of the visible light spectrum: the larger band gap of acidified g-$C_3N_4$ (ACN) captures the blue part of the spectrum, the g-$C_3N_4$ heterojunction ($CN_1/CN_2$) captures the green to yellow portion of the light spectrum, and the smaller band gap of the P3HT, conjugated polymer, captures the red portion of the spectrum, as illustrated in FIG. 3.

The components of the photocatalytic multijunction composite were not only selected to have band gaps that would capture indoor light, but also to have band edges (i.e., valance and conductive band edges) that would maximize photon utilization, and minimize electron-hole recombination. Maximum photon utilization is also achieved by sequencing the assembly of the components with a tight coupling to foster rapid electron transport. Specifically, the materials in the composition were selected and assembled, so the valance and conduction band edges of each component do not allow a backward flow of electrons. The band diagram in FIG. 3 shows a proper upward flow of holes and a downward flow of electrons. This structure assures optimal charge transfer, and a reduced recombination of electrons and holes. Accordingly, there is always continued internal charge transfer. Another critical part of the design is the valance and conduction bands are positioned so the photocatalytic composite splits water through both reduction, with CB above −0.41, and through oxidation, with VB below +0.82.

Figure 4:
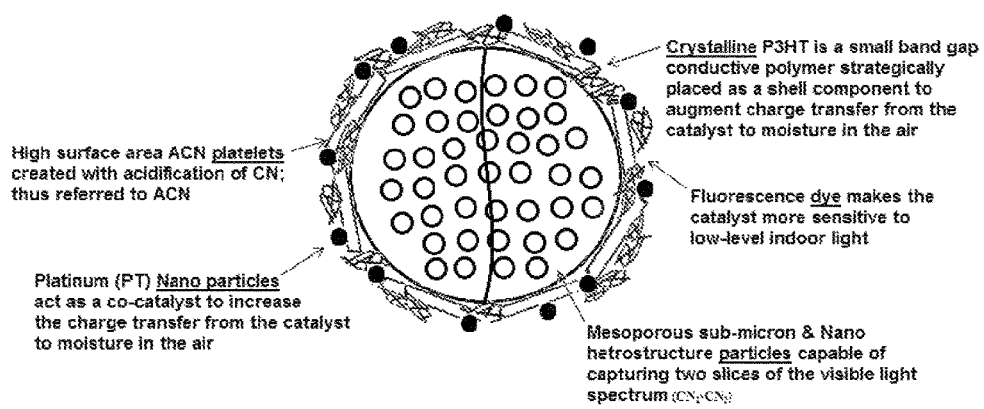
FIG. 4 illustrates the core-shell structure of a photocatalytic composite.

As shown in FIG. 4, P3HT, platinum, and/or fluorescein are strategically placed on the outer edge of the photocatalytic multijunction composite. The photocatalytic multijunction composite was synthesized and assembled with techniques designed to maximize photon utilization. This is achieved by creating a photocatalytic multijunction composite comprising a mixed morphology of mesoporous, sub-micron, nano, crystalline, and platelets components. The preponderance of the components are in the nano and crystalline range, giving rise to high surface areas. High surface areas promote the formation of delocalized π bonds, which enhance the electrical conductivity of each component. In addition, a reduced particle size shortens the distance for the photo-generated electrons to reach the surface. High photon utilization also comes from the components being assembled in a fashion that creates a tight coupling, which assures maximum charge transfer between the components.

Figure 5:
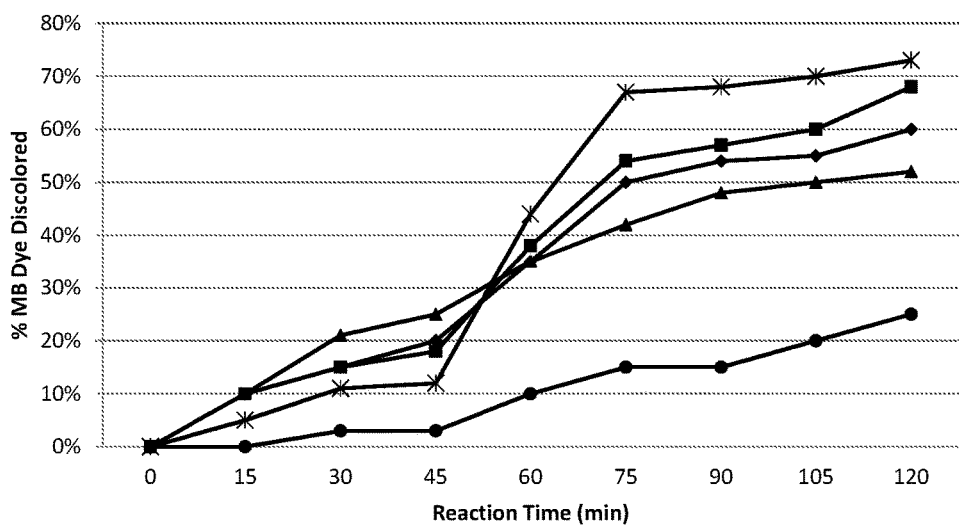
FIG. 5 is a graph of the photocatalytic activity of various photocatalytic components, as measured by reaction time (minutes) versus MB dye discoloration (%). The marker "★" represents Pt/P3HT/ACN/($CN_1/CN_2$); "■" represents P3HT/ACN/($CN_1/CN_2$); "◆" represents ACN/($CN_1/CN_2$); "▲" represents $CN_1/CN_2$ heterojunction; and "●" represents unmodified carbon nitride (CN).

As demonstrated by FIG. 5, each additional component (i.e., a g-$C_3N_4$ heterojunction ($CN_1/CN_2$), acidified g-$C_3N_4$ (ACN), P3HT conjugated polymer, and platinum) increases the photocatalytic activity as measured by the photoreactive composition's ability to degrade methylene blue (MB). The methylene blue (MB) photocatalytic test was performed as follows: To 5 mg of g-$C_3N_4$ powder was added 100 mL methylene blue dye solution with a concentration of 1 g/L. Prior to irradiation with an Xe lamp with a power of 100 mW/$cm^3$, and a wavelength range of 400 nm to 1000 nm, the suspension was stirred in the dark for 45 minutes to reach adsorption equilibrium. The resulting suspension was irradiated with the Xe lamp for 75 minutes (for a total reaction time of 120 minutes, see FIG. 5) under continuous stirring. Aliquots (5 mL) of the suspension were taken out at each 30 minute interval and centrifuged for 10 minutes to obtain the supernatant. The residual concentration of organic dye in the supernatant was measured by a UV-vis spectrophotometer at a maximum absorption wavelength of 665 nm. The percent MB dye discolored was calculated according to:

$$D(\%) = \left(\frac{C_0 - C_t}{C_0}\right) \times 100,$$

wherein $C_0$ is the initial concentration of MB dye and $C_t$ is the residual concentration of MB dye at time (t).

The photoreactive composition comprising acidified g-$C_3N_4$ (ACN), a g-$C_3N_4$ heterojunction ($CN_1/CN_2$), poly (3-hexylthiophene) (P3HT) conjugated polymer, platinum, and fluorescein, as prepared according to Example 1, without a cationic polymer miscible blend was tested against *Clostridium difficile* using the parameters set forth in Table 1, and the results are presented in Table 2.

TABLE 1

Testing Parameters Used for *Clostridium difficile* Study

| Test Substance Size | ~50 mm × 50 mm | Film Used | No |
|---|---|---|---|
| Culture Growth Media | N/A; Spore Prep | Culture Growth Time | Spore Prep |
| Culture Dilution Media | PBS | Culture Dilution Supplement | None |

TABLE 1-continued

Testing Parameters Used for *Clostridium difficile* Study

| | | | |
|---|---|---|---|
| Inoculum Concentration | ~1 × 10⁷ CFU/mL | Inoculum Volume | 0.045 mL |
| Contact Time | 8 hours | Contact Temperature | Ambient |
| Neutralizer | D/E Broth (10 mL) | Enumeration Plate Media | BHIY-HT |
| Enumeration Plate Incubation Time | 36° C. ± 1° C. | Enumeration Plate Incubation Time | 48-72 hours |

TABLE 2

| Test Microorganism | Contact Time | Carrier Type | Replicate CFU/Carrier | Percent Reduction Compared to Control at Contact Time | $Log_{10}$ Reduction Compared to Control at Contact Time |
|---|---|---|---|---|---|
| *Clostridium difficile* ATCC 43598 (Endospores) | T₀ | Control | 2.75 × 10⁷ | N/A | |
| | 8 hours | Control | 2.05 × 10⁷ | N/A | |
| | | Antimicrobial Photoreactive Composition 1 | 9.50 × 10⁵ | 95.37% | 1.33 |

As is apparent from the results set forth in Table 2, the photoreactive composition formed a light activated film that was able to photocatalytically kill 95% of a log 7 (or 27,000,000) population of *Clostridium difficile* in 8 hours. Ordinary room light for these tests was measured at 1200 lux.

Example 3

This example provides an exemplary procedure for the preparation of a photocatalytic multijunction composite that has been modified with $TiO_2$ crystalline nanoparticles. $TiO_2$ enhances the ability of the photocatalytic multijunction composite to capture light in the ultraviolet (UV) range.

Synthesis of the $TiO_2$-photocatalytic multijunction composite begins as outlined in Steps 1-6 of Example 1. To the ACN/(CN₁/CN₂) composite obtained in Step 6 of Example 1 was added 5 nm crystalline $TiO_2$ nanoparticles (30 wt % based on the ACN/(CN₁/CN₂) composite), commercially available from U.S. Research Nanomaterials, Inc. (Houston, Tex.), which had been sonicated in methanol for 5 minutes prior to addition. The composition was mixed for one hour, and the methanol was removed by rotary vacuum. The resulting slurry was dried in an oven at 60° C. overnight, and the remaining powder was calcinated at 400° C. for two hours. The calcinated product was converted into the $TiO_2$-photocatalytic multijunction composite using Steps 7-9 of Example 1.

Figure 6:
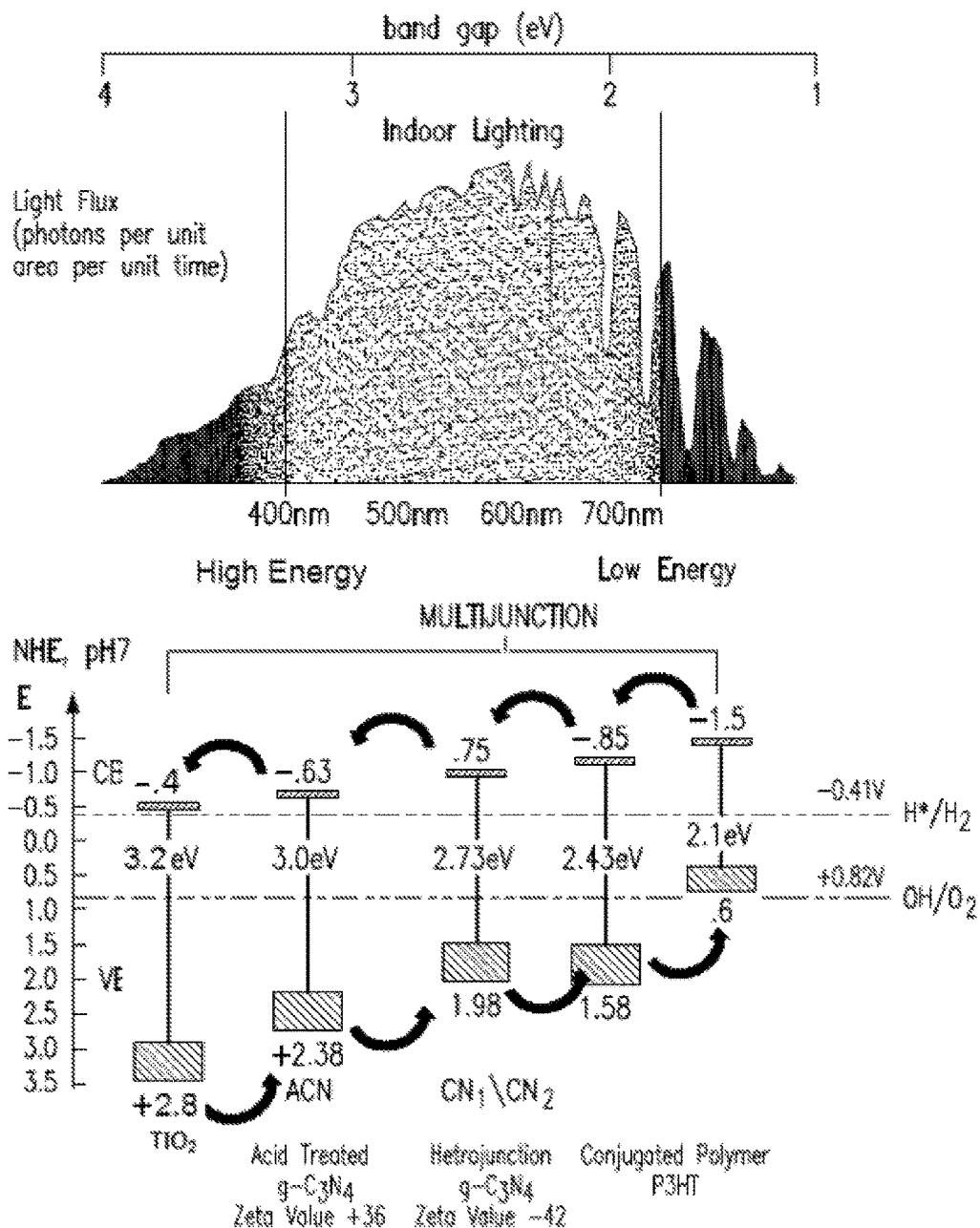
FIG. 6 illustrates the light harvesting ability of a multijunction composite comprising ACN, a $g-C_3N_4$ heterojunction ($CN_1/CN_2$), poly(3-hexylthiophene) (P3HT), and $TiO_2$ crystalline nanoparticles.

As illustrated in FIG. 6, the $TiO_2$-photocatalytic multijunction composite captures three broad slices of the visible light spectrum: the larger band gap of acidified g-$C_3N_4$ (ACN) captures the blue part of the spectrum, the g-$C_3N_4$ heterojunction (CN₁/CN₂) captures the green to yellow portion of the light spectrum, and the smaller band gap of the P3HT, conjugated polymer, captures the red portion of the spectrum, as well as light in the ultraviolet (UV) spectrum (captured by the larger band gap (~3.2 eV) of $TiO_2$).

The materials in the $TiO_2$-photocatalytic multijunction composite were selected and assembled, so the valance and conduction band edges of each component do not allow a backward flow of electrons. FIG. 6 shows a band diagram above shows a proper upward flow of holes and a downward flow of electrons. This structure assures optimal charge transfer, and a reduced recombination of electrons and holes. Accordingly, there is always continued internal charge transfer. Another critical part of the design is the valance and conduction bands are positioned so the photocatalytic composite splits water through both reduction, with CB above −0.41, and through oxidation, with VB below +0.82.

Example 4

This example illustrates a photoreactive composition (Antimicrobial Photoreactive Composition 2) comprising a tungsten-doped $TiO_2$ and g-$C_3N_4$ heterojunction embedded in a cationic film. The cationic film consisted of 6 kppm polyDADMAC complexed with 1.5 kppm of polyacrylic acid and 25 ppm titanate.

The photocatalytic multijunction composite consisting of a tungsten-doped $TiO_2$ and g-$C_3N_4$ heterojunction was prepared using tungsten-doped $TiO_2$ liquid synthesized nano particles, which had been calcined with urea at 400° C. for 1 hour. The resulting poly(amino-tri-s-triazine) polymer (g-$C_3N_4$) with covalently attached $TiO_2$ particles was milled along with powdered urea. The hard material created from calcination is ground into powder so that it can be placed, along with urea, into a planetary ball mill. The mixture was milled at 300 rpm for 30 minutes with 10 wt % urea and balls weighing 10 times the weight of the $TiO_2$. After 30 minutes, the milling drum is three-quarters filled with 200 mL of $H_2O$ and milled an additional 5 minutes to capture and disperse the $TiO_2$ nanoparticles. The contents from the mill were put into a beaker and mixed under 150 W UV light for 1 hour.

The highly dispersed nanopowder was added to the antimicrobial composition. The nanopowder is highly dispersed in water, which keeps it in a non-agglomerated nano state. As such, the functionalization process described herein enables the $TiO_2$ to be dispersible in water, wherein $TiO_2$ is typically only dispersible in alcohol. Creating such a stable nano-dispersion without a surfactant means that when the particles are dispersed into a cationic polymer solution or the PEC, the particles will not be contaminated with a surfactant that could possibly dampen their ability to respond to visible light.

The ability of the resulting antimicrobial photoreactive composition to degrade methylene blue (MB) was tested, and it was observed that the photoreactive compositions significantly degraded the dye within 90 minutes.

The photoreactive composition comprising a tungsten-doped $TiO_2$ and g-$C_3N_4$ heterojunction imbedded in a cationic film was tested against *Clostridium difficile* using the parameters set forth in Table 3, and the results are presented in Table 4.

TABLE 3

Testing Parameters Used for *Clostridium difficile* Study

| | | | |
|---|---|---|---|
| Test Substance Size | 40 mm × 50 mm | Film Used | Yes |
| Culture Growth Media | N/A; Spore Prep | Culture Growth Time | N/A |
| Culture Dilution Media | Reverse Osmosis Water | Culture Dilution Supplement | N/A |
| Inoculum Concentration | ~2 × $10^4$ CFU/mL | Inoculum Volume | 0.020 mL |
| Contact Time | 8 & 16 hours | Contact Temperature | Ambient |
| Neutralizer | D/E Broth (10 mL) | Enumeration Plate Media | BHIY-HT |
| Enumeration Plate Incubation Time | 36° C. ± 1° C. | Enumeration Plate Incubation Time | 48-72 hours |

TABLE 4

| Test Microorganism | Contact Time | Carrier Type | Replicate CFU/Carrier | Percent Reduction Compared to Control at Contact Time | $Log_{10}$ Reduction Compared to Control at Contact Time |
|---|---|---|---|---|---|
| *Clostridium difficile* ATCC 43598 (Endospores) | $T_0$ 8 hours | Control Control Antimicrobial Photoreactive Composition 2 | 2.00 × $10^4$ 2.50 × $10^4$ 3.50 × $10^2$ | N/A N/A 97.67% | N/A N/A 1.63 |

As is apparent from Table 4, a film comprising Antimicrobial Photoreactive Composition 2, under ordinary room light of 1250 lux, was able to inactivate 97.8% of a log 4 *Clostridium difficile* population in 8 hours.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An antimicrobial photoreactive film comprising:
   (a) a photocatalytic multijunction composite blend comprising two or more photocatalytic multijunctions that are not coupled to one another, and
   optionally at least one additive selected from a noble metal, a conjugated polymer, a dye molecule, and a combination thereof,
   wherein at least one of the photocatalytic multijunctions comprises a photocatalytic heterojunction that is primarily carbon based and is selected from graphitic carbon nitride, acidified carbon nitride (ACN), graphene oxide, reduced graphene oxide, a conjugated polymer, and a combination thereof, and
   (b) at least one polymer selected from (b1) and (b2), wherein
   (b1) is a substrate-coupling polymer selected from a branched polyethylenimine-based polymer having carboxylic acid groups, a linear polyethylenimine-based polymer having carboxylic acid groups, a polyethylenimine-based polymer, a cationic block copolymer, a polymer having one or more acyl groups and/or carboxylic acid groups, a salt of any of the foregoing, and a combination thereof, and
   (b2) is at least one cationic polymer selected from a polydiallyldialkylamine-based polymer, an acryloxyalkyltrialkylamine-based polymer, a vinylphenalkyltrialkylamine-based polymer, an acrylamidoalkyltrialkylamine-based polymer, a polyethylenimine-based polymer, and combinations thereof,
   wherein
   the photocatalytic multijunction composite blend is photoreactive at a wavelength from 350 nm and higher and 900 nm and lower,
   the at least one substrate-coupling polymer and/or the at least one cationic polymer forms a film, and the photocatalytic multijunction composite blend is embedded in a film formed by the at least one substrate-coupling polymer and/or the at least one cationic polymer.

2. The antimicrobial photoreactive film of claim 1, wherein the photocatalytic heterojunction that is primarily carbon based comprises acidified carbon nitride (ACN).

3. The antimicrobial photoreactive film of claim 1, wherein the photocatalytic multijunction composite blend comprises at least one photocatalytic heterojunction comprising inorganic material(s) selected from a transition metal oxide, a transition metal sulfide, a transition metal selenide, an alloy comprising copper, indium, gallium, and diselenide (CIGS), and combinations thereof.

4. The antimicrobial photoreactive film of claim 3, wherein the inorganic material(s) are selected from cadmium sulfide (CdS), cadmium selenide (CdSe), an alloy comprising copper, indium, gallium, and diselenide (CIGS), and combinations thereof.

5. The antimicrobial photoreactive film of claim 1, wherein the photocatalytic multijunction composite blend has (i) one or more conduction band(s) more negative than about −0.42 eV at pH 7, (ii) one or more valence band(s) more positive than about +0.81 eV at pH 7, or (iii) both (i) and (ii).

6. The antimicrobial photoreactive film of claim 1, wherein the photocatalytic multijunction composite blend comprises one or more organic material(s) and one or more inorganic material(s), such that a charge transfer from the valence band moves from a less positive potential to a more positive potential, and a charge transfer from the conduction band moves from a higher potential to a lesser negative potential.

7. The antimicrobial photoreactive film of claim 1, wherein the photocatalytic multijunction composite blend photocatalytically oxidizes water to form hydroxy radicals.

8. The antimicrobial photoreactive film of claim 1, wherein the photocatalytic multijunction composite blend photocatalytically reduces water to form superoxide anions.

9. The antimicrobial photoreactive film of claim 1, wherein the photocatalytic multijunction composite blend comprises one or more crystalline components.

10. The antimicrobial photoreactive film of claim 1, wherein the photocatalytic multijunction composite blend comprises one or more platelet component(s).

11. The antimicrobial photoreactive film of claim 1, wherein the photocatalytic multijunction composite blend comprises one or more mesoporous component(s).

12. The antimicrobial photoreactive film of claim 9, wherein the crystalline component blend comprises submicron particles.

13. The antimicrobial photoreactive film of claim 1, wherein the at least one substrate-coupling polymer is a branched polyethylenimine-based polymer having carboxylic acid groups, a linear polyethylenimine-based polymer having carboxylic acid groups, or a combination thereof.

14. The antimicrobial photoreactive film of claim 13, wherein the substrate-coupling polymer is a branched polyethylenimine having carboxylic acid groups.

15. The antimicrobial photoreactive film of claim 1, wherein at least one additive is present in the photocatalytic multijunction composite blend.

16. The antimicrobial photoreactive film of claim 15, wherein the additive is a noble metal selected from ruthenium, rhodium, palladium, silver, osmium, iridium, platinum, gold, and a combination thereof.

17. The antimicrobial photoreactive film of claim 15, wherein the additive is a conjugated polymer selected from poly(3-hexylthiophene) (P3HT), polypyrrole (Ppy), polycarbazole, polyindole, polyazepine, polyaniline, polyfluorene, polyphenylene, polypyrene, polyazulene, polynaphthalene, polythiophene (Ptp), poly(3,4-ethylenedioxythiophene), poly(p-phenylene sulfide), polyacetylene, poly(p-phenylene vinylene), and a combination thereof.

18. The antimicrobial photoreactive film of claim 1, wherein the additive is present and is a dye molecule selected from fluorescein, fluorescein isothiocyanate, a cyanine, a merocyanine, a hemicyanine, a perylene, a xanthene, a porphyrin, a phthalocyanine, a polyene, a polythiophene, a coumarin, a ruthenium-based dye, and a combination thereof.

19. The antimicrobial photoreactive film of claim 1, wherein (b) is (b2) at least one cationic polymer.

20. The antimicrobial photoreactive film of claim 19, wherein the cationic polymer is a linear polyethylenimine-based polymer, polydiallyldimethylammonium chloride (polyDADMAC), poly(acrylamide-co-diallyldimethylammonium chloride), or a combination thereof.

21. The antimicrobial photoreactive film of claim 1, wherein
  (a) the photocatalytic multijunction composite blend comprises acidified graphitic carbon nitride platelets (ACN), a $g$-$C_3N_4$/$g$-$C_3N_4$ heterojunction, and a conjugated polymer, a noble metal, and a fluorescent dye as additives, and
  (b) the substrate-coupling polymer comprises branched polyethylenimine having carboxylic acid groups.

22. The antimicrobial photoreactive film of claim 21, wherein the photocatalytic multijunction composite blend comprises platelets of acidified graphitic carbon nitride, mesoporous submicron and nanoparticles of a $g$-$C_3N_4$/$g$-$C_3N_4$ heterojunction, a crystalline conjugated polymer, and nanoparticles of a noble metal.

23. The antimicrobial photoreactive film of claim 22, wherein the conjugated polymer is crystalline poly(3-hexylthiophene) (P3HT), the noble metal is platinum, and the fluorescent dye is fluorescein.

24. A method of disinfecting a surface of a substrate comprising applying to the surface the antimicrobial photoreactive film of claim 1.

25. The method of claim 24, wherein the film renders the surface of the substrate bactericidal, virucidal, germicidal, and/or fungicidal.

26. The antimicrobial photoreactive film of claim 1, wherein the photocatalytic multijunction composite blend does not comprise a transition metal oxide.

27. The antimicrobial photoreactive film of claim 1, wherein the film is removable from a substrate by a solvent.

28. The antimicrobial photoreactive film of claim 1, wherein the film kills at least 90% of a log 4 population of *Clostridium difficile* (ATCC 43598) bacteria within 24 hours of contact.

* * * * *